(12) United States Patent
Liu et al.

(10) Patent No.: US 9,671,347 B2
(45) Date of Patent: Jun. 6, 2017

(54) METHOD OF DIAGNOSING MALARIA INFECTION IN A PATIENT BY SURFACE ENHANCED RESONANCE RAMAN SPECTROSCOPY

(75) Inventors: Quan Liu, Singapore (SG); Clement Yuen, Singapore (SG)

(73) Assignee: Nanyang Technological University, Singapore (SG)

( * ) Notice: Subject to any disclaimer, the term of this patent is extended or adjusted under 35 U.S.C. 154(b) by 0 days.

(21) Appl. No.: 13/442,594

(22) Filed: Apr. 9, 2012

(65) Prior Publication Data

US 2012/0257199 A1 Oct. 11, 2012

Related U.S. Application Data

(60) Provisional application No. 61/473,351, filed on Apr. 8, 2011.

(51) Int. Cl.
*G01N 21/65* (2006.01)

(52) U.S. Cl.
CPC .................. *G01N 21/658* (2013.01)

(58) Field of Classification Search
CPC .................................. G01N 21/658
USPC ........................................ 356/301
See application file for complete search history.

(56) References Cited

U.S. PATENT DOCUMENTS

| 8,385,997 B2 * | 2/2013 | Hyde et al. ............. 600/318 |
| 2008/0305489 A1 * | 12/2008 | Thomas et al. ............. 435/6 |
| 2009/0317802 A1 * | 12/2009 | Bhatia et al. ............. 435/6 |
| 2010/0222662 A1 * | 9/2010 | Hegg et al. ............. 600/407 |
| 2013/0040292 A1 * | 2/2013 | Fernandez Lopez et al. ............. 435/6.11 |

FOREIGN PATENT DOCUMENTS

ES WO2007034021 * 3/2007 ........... G01N 33/552

OTHER PUBLICATIONS

Akins et al., "Aggregation-enhanced raman scattering of a cyanine dye in homogeneous solution", *J. Phys. Chem. A* 101(18):3251-9, 1997. 9 Pages.

Aoki et al., "Coupling surface-enhanced resonance raman scatting and electronic tongue as characterization tools to investigate biological membrane mimetic systems", *Anal. Chem.* 82:3537-46, 2010. 10 Pages.

Bizzari et al., "SERS and tunneling spectroscopy investigation of iron-protoporphyrin IX adsorbed on a silver tip", *J. Phys. Chem. B* 109(35):16571-4, 2005. 4 Pages.

Blauer et al., "Investigations of B- and β-hematin", *J. Inorg. Biochem.* 66(2):145-52, 1997. 8 Pages.

(Continued)

*Primary Examiner* — Tarifur Chowdhury
*Assistant Examiner* — Omar Nixon
(74) *Attorney, Agent, or Firm* — Seed IP Law Group LLP

(57) ABSTRACT

Present disclosure relates to a method of diagnosing malaria infection in a patient by Surface Enhanced Raman Spectroscopy (SERS). The method includes obtaining a sample from said patient, mixing the sample with a suspension of magnetic nanoparticles, wherein said magnetic nanoparticles adsorb hemozoin present in the sample onto their surface, obtaining the SERS spectra of the sample, and correlating the obtained SERS spectra to the presence or amount of hemozoin in the sample, wherein the presence of hemozoin is indicative of malaria infection.

9 Claims, 10 Drawing Sheets

(56) References Cited

OTHER PUBLICATIONS

Bohle et al., "structural and spectroscopic studies of β-hematin (the heme coordination polymer in malaria pigment)", *ACS Symp. Ser.* 572:497-515, 1994. 19 Pages.

Charm et al., "Synthesis of surface enhanced raman scattering active magnetic nonparticles for cell labeling and sorting", *J. Appl. Phys.* 105:07B310, 2009. 4 Pages.

Cinta-Pinzaru et al., "FT-raman and NIR-SERS characterization of the antimalarial drugs chloroquine and mefloquine and their interaction with hematin", *J. Raman Spectrosc.* 37:326-34, 2006. 9 Pages.

Demirev et al., "Detection of malaria parasites in blood by laser desorption mass spectrometry", *Anal Chem.* 74(14):3262-6, 2002. 5 Pages.

Ebner et al., "Magnetic field orientation and spatial effects on the retention of paramagnetic nanoparticles with magnetite", *Sep. Purif. Technol.* 37(16):3727-3752, 2002. 27 Pages.

Egan et al., "The mechanism of β-hematin formation in acetate solution. Parallels between hemozoin formation and biomineralization processes", *Biochemistry* 40:204-13, 2001. 10 Pages.

Frosch et al., "In situ localization and structural analysis of the malaria pigment hemozoin", *J. Phys. Chem. B* 111(37):11047-56, 2007. 10 Pages.

Gao et al., "Multifunctional magnetic nanoparticles: design, synthesis, and biomedical applications", *Acc. Chem. Res. B* 42(8):1097-1107, 2009. 11 Pages.

Goya et al., "Static and dynamic magnetic properties of spherical magnetite nanoparticles", *J. Appl. Phys.* 94(5):3520-8, Sep. 1, 2003. 10 Pages.

Heider et al., "Magnetic susceptibility and remanent coercive force in grown magnetite crystals from 0.1 μm to 6 mm", *Phys. Earth Planet In.* 93:239-256, 1996. 18 Pages.

Holligan et al., "Magnetic guidance of ferrofluidic nanoparticles in an in vitro model of intraocular retinal repair", *Nanotechnology* 14:661-6, 2003. 6 Pages.

Hu et al., "Assignment of protoheme resonance raman spectrum by heme labeling in myoglobin", *J. Am. Chem. Soc.* 118:12638-46, 1996. 9 Pages.

Kim et al, "Improved methods for magnetic purification of malaria parasites and haemozoin", *Malar. J.* 9(17):1-5, Jan. 14, 2010. 5 Pages.

Kneipp et al., "Ultrasensitive chemical analysis by raman spectroscopy", *Chem. Rev.* 99(10):2957-75, 1999. 19 Pages.

Laurent et al., "Magnetic iron oxide nanoparticles: synthesis, stabilization, vectorization, physicochemical characterizations, and biological applications", *Chem. Rev.* 108(6):2064-10, 2008. 47 Pages.

Lee et al., "Surface-enhanced raman spectroscopy and nanogeometry: the plasmonic origin of SERS", *J. Phys. Chem. C* 111(49):17985-8, 2007. 4 Pages.

Moody et al., "Rapid diagnostic tests for malaria parasites", *Clin. Microbiol. Rev.* 15(1):66-78, Jan. 2002. 13 Pages.

Moore et al., "Hemoglobin degradation in malaria-infected erythrocytes determined from live cell magnetophoresis", *FASEB J.* 20:747-9, Apr. 2006. 3 Pages.

Mungai et al., "Transfusion-transmitted malaria in the United States from 1963 through 1999", *N. Engl. J. Med.* 344(26):1973-8, Jun. 28, 2001. 6 Pages.

Murray et al., "Update on rapid diagnostic testing for malaria", *Clin. Microbiol. Rev.* 21(1):97-110, Jan. 2008. 14 Pages.

Newman et al., "A magneto-optic route toward the in vivo diagnosis of malaria: preliminary results and preclinical trial data", *Biophys. J.* 95:994-1000, Jul. 2008. 7 Pages.

Noland et al., "The shape and size of hemozoin crystals distinguishes diverse *Plasmodium* species", *Mol. Biochem. Parasitol.* 130:91-99, 2003. 9 Pages.

Pagola et al., "The structure of malaria pigment β-haematin", *Nature* 404:307-10, Mar. 16, 2000. 6 Pages.

Schindler et al., "Development and optimization of polymerase chain reaction-based malaria diagnostic methods and their comparison with quantitative buffy coat assay", *Am. J. Trop. Med. Hyg.* 65(4):355-61, 2001. 7 Pages.

Serebrennikova et al., "Interpretation of the ultraviolet-visible spectra of malaria parasite *Plasmodium falciparum*", *Appl. Opt.* 49(2):180-8, Jan. 10, 2010. 9 Pages.

Shapiro et al., "Cytometry in malaria: moving beyond giemsa", *Cytometry A* 71(9):643-5, 2007. 3 Pages.

Tangpukdee et al., "Malaria diagnosis: a brief review", *Korean J. Parasitol.* 47(2):93-102, Jun. 2009. 10 Pages.

Urbach et al., "Sub-100 nm confinement of magnetic nanoparticles using localized magnetic field gradients", *J. Am. Chem. Soc.* 125(42):12704-5, 2003. 2 Pages.

Weissbuch et al., "Interplay between malaria, crystalline hemozoin formation, and antimalarial drug action and design", *Chem. Rev.* 108(11):4899-4914, 2008. 16 Pages.

World Health Organization, "World malaria report 2009", 2009. 78 Pages.

World Health Organization, "World malaria report 2010", 2010. 238 Pages.

Wood et al., "Resonance raman spectroscopy reveals new insight into the electronic structure of β-hematin and malaria pigment", *J. Am. Chem. Soc.* 126(30):9233-9, 2004. 7 Pages.

Wu et al., "Visual detection of Sudan dyes based on the Plasmon resonance light scattering signals of silver nanoparticles", *Anal. Chem.* 78(15):5570-7, Aug. 1, 2006. 8 Pages.

Xu et al., "Synthesis and utilization of monodisperse superparamagnetic colloidal particles for magnetically controllable photonic crystals", *Chem. Mater.* 14(3):1249-56, 2002. 8 Pages.

Yuen et al, "Improving surface-enhanced raman scattering effect using gold-coated hierarchical polystyrene bead substrates modified with postgrowth microwave treatment", *J. Biomed. Opt.* 13(6):064040, Nov./Dec. 2008. 7 Pages.

Yuen et al., "Low-level detection of anti-cancer drug in blood plasma using microwave-treated gold-polystyrene beads as surface-enhanced raman scattering substrates", *Biosensors and Bioelectronics* 26:580-4, 2010. 5 Pages.

Yuen et al., "Optimization of extinction efficiency of gold-coated polystyrene bead substrates improves surface-enhanced raman scattering effects by post-growth microwave heating treatment", *J. Raman Spectrosc.* 41:375-80, 2010. 7 Pages.

Zhai et al., "Fabrication of iron oxide core/gold shell submicrometer spheres with nanoscale surface roughness for efficient surface-enhanced raman scattering", *J. Phys. Chem. C* 113(17):7009-14, 2009. 6 Pages.

Zhou et al., "In situ nucleation and growth of silver nanoparticles in membrane materials: a controllable roughened SERS substrate with high reproducibility", *J. Raman Spectrosc.* 40:31-37, 2009. 7 Pages.

* cited by examiner

METHOD OF DIAGNOSING MALARIA INFECTION IN A PATIENT BY SURFACE ENHANCED RESONANCE RAMAN SPECTROSCOPY

CROSS-REFERENCE TO RELATED APPLICATION

This application claims the benefit of priority of U.S. Provisional Patent Application No. 61/473,351, filed 8 Apr. 2011, the contents of which being hereby incorporated by reference in its entirety for all purposes.

TECHNICAL FIELD

The disclosure relates to a method of diagnosing malaria infection in a patient by Surface Enhanced Raman Spectroscopy (SERS) using magnetic nanoparticles, and in particular, to a method of diagnosing malaria infection in a patient by Surface Enhanced Resonance Raman Spectroscopy (SERRS) using magnetic nanoparticles.

BACKGROUND

Human malaria disease is a worldwide disease with estimated 225 million cases, accounting for 800,000 deaths per year. This disease is caused by a parasite protozoan, in which the parasite infects red blood cells of the host and hemozoin biocrystals are disposed as by-products after the ingestion of haemoglobins. Since the malaria disease can aggravate into a fatal illness within hours upon development of the first symptom, the early diagnosis of malaria infection is important, which requires the detection of hemozoin at low concentrations in infected blood cells.

Malaria disease control, including both diagnosis and treatment, has thus become an important global health issue. Since effective drugs for malaria treatment have not been developed, early malaria diagnosis is important in the malaria disease control to curtail morbidity, mortality and transmission of malaria, by prompting early treatment and cure of malaria infection.

In malaria diagnosis, microscopic examination of blood smears remains the "gold standard" for the detection of malaria parasite, but this method is labour-intensive and time-consuming. Moreover, it requires special expertise from operators for reliable data interpretation.

Recently, several other malaria diagnosis techniques, such as the quantitative buffy coat method, molecular diagnostic method, flow cytometry technique, serological tests, and laser desorption mass spectrometry, have been developed to address these shortcomings. Among these methods, Resonance Raman Spectroscopy (RRS) has been reported to amplify the Raman signal of dried β-hematin crystals by the close Raman shift matching of the laser source and electronic transition of β-hematin. It has been found that β-hematin crystals, which are synthetic forms of hemozoin biocrystals, are similar to hemozoin biocrystals in molecular structure and thus have Raman signals equivalent to hemozoin. Hence, improved methods for the detection of β-hematin, may similarly be applied to improve hemozoin detection and thus, since the presence of hemozoin is indicative of malaria infection, malaria diagnosis.

Besides RRS, Surface Enhanced Raman Spectroscopy (SERS) has also been shown to enhance the Raman spectrum of hematin (soluble form of β-hematin) at $1\times10^{-5}$ M via the augmented electromagnetic coupling between hematin and gold or silver nanoparticles.

Although the above methods show promise in the detection of hemozoin, the presence of hemozoin at low concentrations in the early stages of malaria infection, where in the ring stage for instance the concentration can be less than $1\times10^{-5}$ M, renders the RRS and SERS methods insufficient for an effective detection of hemozoin in the earlier stage of malaria infection.

Therefore, there remains a need to develop a more sensitive detection technique, which requires minimal labor and expertise for hemozoin detection, particularly in the diagnosis of early stage malaria infection where concentration of hemozoin may be $1\times10^{-5}$ M or less.

SUMMARY

In a first aspect, there is provided a method of diagnosing malaria infection in a patient by Surface Enhanced Raman Spectroscopy (SERS). The method includes:
  obtaining a sample from said patient;
  mixing the sample with a suspension of magnetic nanoparticles, wherein said magnetic nanoparticles adsorb hemozoin present in the sample onto their surface;
  obtaining the SERS spectra of the sample; and
  correlating the obtained SERS spectra to the presence or amount of hemozoin in the sample, wherein the presence of hemozoin is indicative of malaria infection.

In various embodiments, the method further relies on the success in detecting the RRS and SERS signal of hemozoin which shows the potential for further augmentation by combining the two effects, known as surface enhanced resonance Raman spectroscopy (SERRS).

Accordingly, the present disclosure provides a novel magnetic field enrichment strategy on SERRS by using magnetic nanoparticles to augment Raman signals from β-hematin crystals, similar to hemozoin in molecular, magnetic and Raman properties. The SERRS effect is further enhanced by the magnetic enrichment of β-hematin crystals and magnetic SERS-active nanoparticles with iron oxide core and silver shell. The performance of magnetic field-enriched SERRS quantified experimentally is compared with that of the SERRS without the influence of magnetic field, and the ordinary RRS on β-hematin crystals. Furthermore, the analytical enhancement factor and sensitivity of the proposed magnetic field-enriched SERRS technique are investigated.

BRIEF DESCRIPTION OF THE DRAWINGS

In the drawings, like reference characters generally refer to the same parts throughout the different views. The drawings are not necessarily drawn to scale, emphasis instead generally being placed upon illustrating the principles of various embodiments. In the following description, various embodiments of the disclosure are described with reference to the following drawings.

DESCRIPTION

Figure 1:
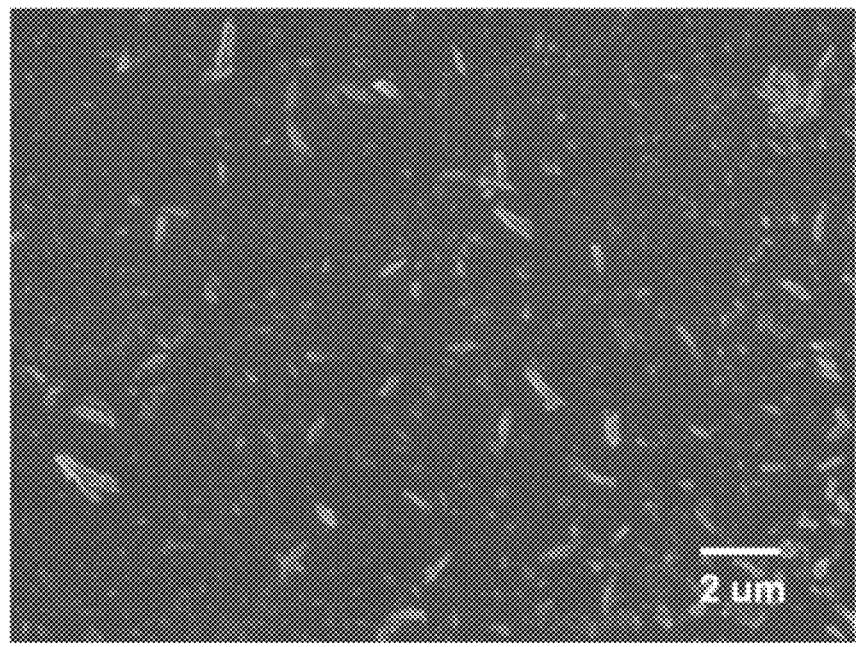
FIG. 1 shows a field emission scanning electron microscope image (FESEM) of β-hematin crystals synthesized in accordance with Example 1.

The following detailed description refers to the accompanying drawings that show, by way of illustration, specific details and embodiments in which the disclosure may be practised. These embodiments are described in sufficient detail to enable those skilled in the art to practise the disclosure. Other embodiments may be utilized and changes may be made without departing from the scope of the disclosure. The various embodiments are not necessarily mutually exclusive, as some embodiments can be combined with one or more other embodiments to form new embodiments.

Compared to ordinary Raman spectroscopy, Surface Enhanced Raman Spectroscopy (SERS) has been demonstrated and proven to enable further enhancement in the Raman signal of test molecules or analytes adsorbed on metal surfaces. While this technique shows promise for further augmentation in Raman signals, certain analytes, for example, hemozoin or β-hematin crystals, are difficult to be adsorbed on metal surfaces for effective enhancement in sensitive detection.

Thus, according to one aspect of the disclosure, a method of diagnosing malaria infection in a patient by Surface Enhanced Raman Spectroscopy is provided.

In the present context, Surface Enhanced Raman Spectroscopy, also known as Surface Enhanced Raman Scattering, abbreviated SERS, is a surface sensitive technique that results in the enhancement of Raman scattering by molecules adsorbed on metal surfaces. The enhancement factor can be as much as $10^{14}$ to $10^{15}$, which allows the technique to be sensitive enough to detect single molecules.

The term "detect", "detecting", or "detection", as used herein refers to a method of verifying the presence of a given molecule or analyte. The detection may also be quantitative, i.e. include correlating the detected signal with the amount of analyte. The detection includes in vitro as well as in vivo detection.

The present method includes obtaining a sample from the patient. The term "sample", as used herein, refers to an aliquot of material, frequently biological matrices, an aqueous solution or an aqueous suspension derived from biological material. Samples to be assayed for the presence of an analyte by the methods of the present disclosure include, for example, fluids, cells, tissues, homogenates, lysates, extracts, and purified or partially purified proteins and other biological molecules and mixtures thereof.

Non-limiting examples of samples typically used in the methods of the disclosure include human and animal body fluids such as whole blood, serum, plasma, cerebrospinal fluid, sputum, bronchial washing, bronchial aspirates, urine, semen, lymph fluids and various external secretions of the respiratory, intestinal and genitourinary tracts, tears, saliva, milk, white blood cells, myelomas and the like; biological fluids such as cell culture supernatants; tissue specimens which may or may not be fixed; and cell specimens which may or may not be fixed. The samples used in the methods of the present disclosure will vary based on the assay format and the nature of the tissues, cells, extracts or other materials, especially biological materials, to be assayed. Methods for preparing protein extracts from cells or samples are well known in the art and can be readily adapted in order to obtain a sample that is compatible with the methods of the disclosure. Detection in a body fluid can also be in vivo, i.e. without first collecting a sample.

Before assaying the sample, one or more optional sample purification steps can be performed. Such purification can for example be used to separate cells and cell debris from a fluid sample that is to be assayed. Various suitable purification methods are known to those skilled in the art and include, without limitation, centrifugation, chromatography, precipitation, filtration and the like.

In various embodiments, the sample that is obtained from the patient infected with malaria contains a pigment called hemozoin, which is a crystalline product of the digestion of heme molecules by the malaria parasites. It is the presence of hemozoin which is relied upon as the detection mechanism of the present disclosure.

β-hematin crystals refer to a synthetic form of hemozoin, and may be synthesized using an acid-catalysed method (Egan et al., *Biochemistry*, "*The mechanism of β-hematin formation in acetate solution. Parallels between hemozoin formation and biomineralization process*", 2001, 40, 204-213). They are synthesized in the laboratory to simulate hemozoin behavior, in particular, with regard to their spectroscopic properties, as β-hematin crystals and hemozoin have similar molecular structures and therefore exhibit equivalent fingerprints in Raman spectroscopic methods, such as Surface Enhanced Raman Spectroscopy (SERS), Surface Enhanced Raman Resonance Spectroscopy (SERRS), and Resonance Raman Spectroscopy (RRS).

The sample that is obtained from the patient is contacted with a suspension of magnetic nanoparticles.

In present context, a "nanoparticle" refers to a particle having a characteristic length, such as diameter, in the range of up to 500 nm. Nanoparticles suitable for use in a SERS-based detection method include nanoparticles that comprise a SERS active metal. Examples of a SERS active metal include, but are not limited to, noble metals such as silver, palladium, gold, platinum, iridium, osmium, rhodium, ruthenium, and alloys thereof, and copper. In various embodiments, the SERS active metal in the nanoparticles is silver (Ag).

Magnetic nanoparticles are a class of nanoparticle which can be manipulated using magnetic field. Such particles commonly include or consist of magnetic elements or magnetic materials such as iron, nickel, and cobalt, and their respective chemical compounds. In various embodiments, the magnetic materials in the magnetic nanoparticles are iron (II, III) oxide, abbreviated $Fe_3O_4$.

The magnetic nanoparticles may be irregular or regular in shape. In some embodiments, the magnetic nanoparticles are regular in shape. For example, the magnetic nanoparticles may have a regular shape such as a sphere, a cube or a tetrahedron. Accordingly, the nanoparticles may be nanospheres, nanocubes or nanotetrahedra.

The size of the nanoparticles may be characterized by their mean diameter. The term "diameter" as used herein refers to the maximal length of a straight line segment passing through the center of a figure and terminating at the periphery. Accordingly, the term "mean diameter" refers to an average diameter of the nanoparticles, and may be calculated by dividing the sum of the diameter of each nanoparticle by the total number of nanoparticles. Although the term "diameter" is used normally to refer to the maximal length of a line segment passing through the centre and connecting two points on the periphery of a nanosphere, it is also used herein to refer to the maximal length of a line segment passing through the centre and connecting two points on the periphery of nanoparticles having other shapes, such as a nanocube or a nanotetrahedra.

In various embodiments, the diameter of the nanoparticles used according to the present disclosure is in the range of between 1 and 200 nm, preferably between 10 and 70 nm, more preferably about 40 to 60 nm. The particles are preferably substantially monodisperse.

In various embodiments, the magnetic nanoparticles have a core-shell structure, in which the core of the magnetic nanoparticles comprises a magnetic material and the shell of the magnetic nanoparticles comprises a SERS active metal. In various embodiments, the core of the magnetic nanoparticles consists substantially of a magnetic material and the shell of the magnetic nanoparticles consists substantially of a SERS active metal. The magnetic material and the SERS active metal can be as defined above. As mentioned herein, the SERS active metal may be a noble metal, such as silver. In one specific embodiment, the magnetic nanoparticles are formed of a $Fe_3O_4$ core and a Ag shell (abbreviated as $Fe_3O_4$@Ag).

The shell surrounding the magnetic nanoparticles may have a substantially uniform thickness. The shell may have any suitable thickness that allows a SERS signal to be obtained and does not unduly affect the magnetic effects of the nanoparticle core on the adsorption of the hemozoin. In various embodiments, the thickness of the shell is less than about 50 nm, such as about 1 nm to about 20 nm, or about 5 nm to about 10 nm, or about 50 nm.

In certain embodiments where the magnetic nanoparticles comprise a core-shell structure and are spherical in shape, the mean diameter of the magnetic nanoparticles may be about 60 nm based on an approximately 50 nm core and an approximately 5 nm thick shell surrounding the core. In other embodiments, the mean diameter of the magnetic nanoparticles may be about 150 nm based on an approximately 50 nm core and an approximately 50 nm thick shell surrounding the core.

In certain embodiments, the magnetic nanoparticles comprise $Fe_3O_4$@Ag. In one embodiment, the $Fe_3O_4$@Ag nanoparticles are synthesized using a seed-growth reduction method (Charan et al., *J. Appl. Phys.*, "*Synthesis of surface enhanced Raman scattering active magnetic nanoparticles for cell labeling and sorting*", 2009, 105, 07B310) described in Example 1 and Example 2 below.

In mixing the sample with the suspension of magnetic nanoparticles, the magnetic nanoparticles physically adsorb hemozoin present in the sample onto their surface due to their surface energy properties. The adsorption is enhanced with the application of an external field.

In present context, the term "mixing" as used herein refers generally to providing access of one component, reagent, analyte or sample to another. For example, in this instance, mixing can involve adding the sample to the suspension of magnetic nanoparticles. Alternatively, mixing can involve adding the suspension of magnetic nanoparticles to the sample. Unless otherwise stated, the order of adding one component to another component generally does not affect the working of the disclosure.

The method further includes obtaining the SERS spectra of the sample. In various embodiments, obtaining the SERS spectra of the sample includes exciting the sample with a laser source. The Raman scattering effect occurs when light impinges upon a molecule and interacts with the electron cloud and the bonds of that molecule. During the process, a photon excites the molecule from the ground state to a virtual energy state. When the molecule relaxes it emits a photon and returns to a different rotation or vibrational state. The difference in energy between the original state and this new state leads to a shift in the emitted photon's frequency away from the excitation wavelength. If the final vibrational state of the molecule is more energetic than the initial state, then the emitted photon will be shifted to a lower frequency in order for the total energy of the system to remain balanced. Raman scattering is an example of inelastic scattering because of the energy transfer between the photons and the molecules during their interaction.

Generally, exciting the sample with a laser source includes irradiating the sample including the magnetic nanoparticles with a laser source. The excitation period may be less than about one minute, such as less than about 45 seconds, less than about 30 seconds, or less than about 15 seconds. In one embodiment, the excitation period may be about 15 seconds.

Generally, any UV, VIS, or NIR laser with a narrow laser line may be used. In various embodiments, the excitation laser has a wavelength of about 400 nm to about 1,100 nm, such as about 488 nm, about 532 nm, about 633 nm, about 635 nm, about 647 nm, about 785 nm, about 830 nm, or about 1064 nm. In one embodiment, the excitation wavelength is about 633 nm. In certain embodiments, the excitation laser is tunable with respect to the wavelength (or frequency).

In various embodiments, the excitation laser has an output power of about 0.1 mW and more, for example, about 0.1 mW, about 1 mW, about 2 mW, about 5 mW, about 10 mW, about 12 mW, about 15 mW, about 18 mW, about 20 mW, or about 22 mW. In one embodiment, the excitation laser has a power of about 0.1 mW.

The method of diagnosing malaria infection in a patient by SERS according to the present disclosure comprises diagnosing malaria infection in a patient by Surface Enhanced Resonance Raman Spectroscopy (SERRS). SERRS refers to a form of SERS, in which the detection method is based on the effect of two processes, namely, resonance Raman scattering and SERS. In such embodiments, when the analyte is adsorbed on the magnetic nanoparticles surface and is used in combination with the laser frequency close to the frequency of an electronic transition of the analyte, large enhancements in signals can be observed. This increase can be as much as 6 orders of magnitude over normal Raman scattering. The resonance effect takes place when the excitation laser frequency is chosen in a way that it crosses frequencies of electronic excited states and resonates with them. Thus, in certain embodiments, the method includes exciting the sample with a laser source having a resonant wavelength for hemozoin.

In certain embodiments, the adsorption of analyte molecules on metal surfaces can be improved by using magnetic nanoparticles, e.g. nanoparticles made of iron oxide that has been shown to be effective magnets at room temperature, to attract hemozoin which is paramagnetic in the presence of an external magnetic field.

In various embodiments, prior to obtaining the SERS spectra of the sample, the sample and suspension of magnetic nanoparticles are subjected to a magnetic field. In alternative embodiments, the sample and suspension of magnetic nanoparticles are subjected to a magnetic field during excitation with a laser source. Additionally, in various embodiments, the sample and suspension of magnetic nanoparticles are subjected to a magnetic field prior to and during excitation with a laser source.

By subjecting the sample to a magnetic field, hemozoin are enriched. The enrichment of β-hematin concentrations due to a magnetic field can be interpreted by the fact that paramagnetic β-hematin are attracted much faster to the bottom of the vial by the magnet than unmagnetized crystals without the influence of a magnetic field. Consequently, the concentration of β-hematin will be higher at the laser spot than that without the magnetic field. In addition, more nanoparticle-hematin aggregates are formed by an external magnetic field. In addition, the external magnetic field may magnetize hemozoin, such that the average distance between $Fe_3O_4$@Ag nanoparticles and hemozoin may be reduced, which results in a stronger surface enhancement. Furthermore, as a result of the enriching effect by the external magnetic field, there may be an increased number of $Fe_3O_4$@Ag nanoparticles available for binding to hemozoin. The benefits of the application of an external magnetic field are discussed in greater details in Example 3 below.

In various embodiments, the sample is subjected to a magnetic field of about 2 T or less, such as about 0.198 T, about 0.195 T, about 0.190 T, about 0.185 T, or about 0.180 T. In one embodiment, the sample is subjected to a magnetic field of about 0.198 T and a magnetic field gradient of about 26.6 T/m.

The method also includes correlating the obtained SERS spectra to the presence or amount of hemozoin in the sample, wherein the presence of hemozoin is indicative of malaria infection. The amount of hemozoin detected in the sample may also be correlated to the stage of the malaria infection. As an illustration, a hemozoin concentration of about 0.22 pg/cell in the earlier malaria infection at the ring stage and a molecular weight of 1229 g/mol at the early stage were demonstrated in Example 3.

The spectrum of the Raman-scattered light depends on the molecular constituents present and their state, allowing the spectrum to be used for material identification and analysis. This unique characteristic is being made use of by comparing and correlating the obtained SERS spectra with the SERS spectra of known molecules to determine the presence or amount of hemozoin in the sample. In various embodiments, prominent vibrational features, such as $v_8$ (based on the electron spin and crystallographic coordination notation tetragonal $D_{4h}$ system for resonance Raman peaks studies on myoglobin) at 345 $cm^{-1}$, $\gamma_6$ at 367 $cm^{-1}$, $v_{15}$ at 754 $cm^{-1}$, $v_{22}$ at 1120 $cm^{-1}$, $v_{11}$ at 1551 $cm^{-1}$, $v_2$ at 1570 $cm^{-1}$, and $v_{10}$ at 1628 $cm^{-1}$, are noted in most of the spectra. The locations of these peaks are equal to those reported Raman peaks for hemozoin biocrystals (Frosch, T; Koncarevic, S.; Zedler, L.; Schmitt, M.; Schenzel, K.; Becker, K.; Popp, J., "*In situ localization and structural analysis of the malaria pigment hemozoin*", *J. Phys. Chem. B* 2007, 111, (37), 11047-11056), confirming that the spectral features of β-hematin crystals are equivalent to hemozoin in Raman studies, and therefore indicative of the presence of hemozoin in the sample (see Example 3 below).

In a second aspect, there are provided magnetic nanoparticles comprising hemozoin adsorbed to surface thereof. Suitable magnetic nanoparticles that may be used have already been described herein. For example, the magnetic nanoparticles may have a core-shell structure. In various embodiments, the magnetic nanoparticles comprise a $Fe_3O_4$ core and an Ag shell. The magnetic nanoparticles comprising hemozoin adsorbed to surface thereof may be used in a method to diagnose malaria infection in a patient by Surface Enhanced Raman Spectroscopy (SERS).

In order that the disclosure may be readily understood and put into practical effect, particular embodiments will now be described by way of the following non-limiting examples.

EXAMPLES

Example 1

Magnetic Field-Enriched SERS

In this example, magnetic nanoparticles with silver shell have been shown to enhance the Raman signal of β-hematin by a few orders of magnitude under the influence of a magnetic field, showing great potential for use in malaria diagnosis.

Materials and Methods

Synthesis of β-Hematin

The β-hematin crystals were synthesized by using an acid-catalyzed method (Egan et al., *Biochemistry*, "The mechanism of β-hematin formation in acetate solution. Parallels between hemozoin formation and biomineralization process", 2001, 40, 204-213). In a constant temperature bath of 60° C. with constant stirring (about 150 rpm), Ferriprotoporphyrin IX was added to sodium hydroxide (NaOH) of 0.1 M, followed by the introduction of hydrochloric acid (HCl) (0.1 M) to neutralize the alkaline mixture within 10 minutes. After another 3 minutes a sodium acetate buffer solution (4.5 M) with a pH of 4.5 was added into the mixture to maintain an appropriate pH for reaction. The mixture was allowed to react for 60 min prior to being washed with deionized water and filtered. The residue from filtration was collected and dried over phosphorus pentoxide ($P_2O_5$) for ~48 hr.

Synthesis of $Fe_3O_4$@Ag Nanoparticles

A seed-growth reduction method (Charan et al., 2009, supra.) was used to fabricate nanoparticles with $Fe_3O_4$ core and Ag shell ($Fe_3O_4$@Ag). Purchased $Fe_3O_4$ magnetic nanoparticles (diameter of ~50 nm) were mixed with an $AgNO_3$ solution (Ag salt concentration of $1.77\times10^{-4}$ M and shaken for 30 min, prior to the addition of hydroxylamine hydrochloride to reduce Ag salt for another 5 min. An $AgNO_3$ solution with an Ag salt concentration of $1.77\times10^{-4}$ M was added again to the mixture to ensure growth of Ag on Ag seeds formed on each $Fe_3O_4$ core during the first $AgNO_3$ addition and allowed to react for 10 min with vigorous shaking. The final mixture was collected by a magnet and washed with deionized water.

Raman Instrumentation

A 785 nm-laser was used to excite all the samples. Excitation power of 20 mW and 2 mW, respectively, were employed for the study of β-hematin based on ordinary Raman spectroscopy and SERS.

Results

FIG. 1 gives the field emission scanning electron microscope (FESEM) image of fabricated β-hematin. Each β-hematin crystal shows to be elongated with a typical dimension of about 1 um×200 nm. The crystals have distinguishable facets and show an external appearance resembling hemozoin biocrystals reported in the literature (Noland et al., *Mol. Biochem. Parasitol.*, "The shape and size of hemozoin crystals distinguishes diverse Plasmodium species", 2003, 130, 91-99).

Figure 2:
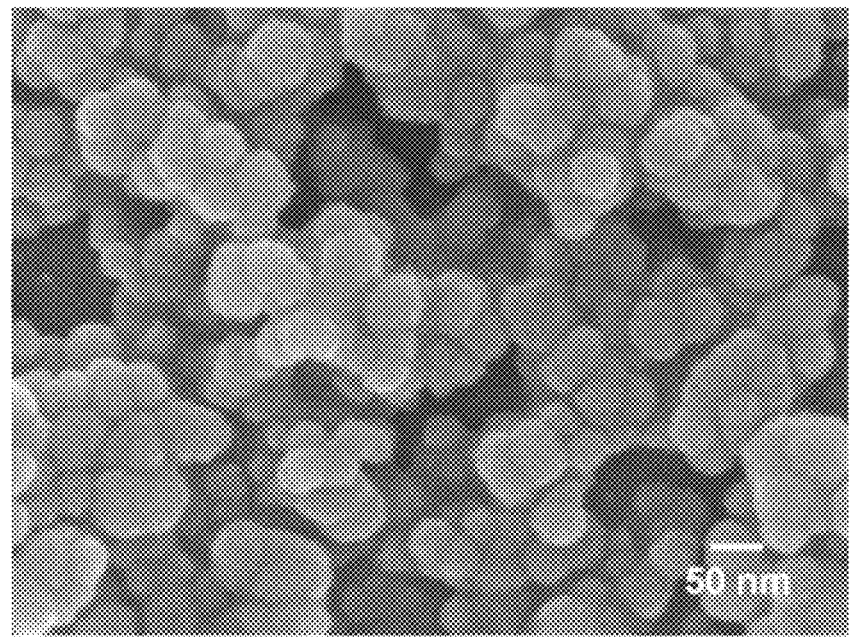
FIG. 2 shows a FESEM image of magnetic nanoparticles having a $Fe_3O_4$ core and an Ag shell (herein abbreviated as $Fe_3O_4$@Ag nanoparticles) synthesized in accordance with Example 1.

FIG. 2 illustrates the FESEM image of the $Fe_3O_4$@Ag nanoparticles. The $Fe_3O_4$@Ag nanoparticles are circular in shape with a mean diameter of about 60 nm. Thus, the Ag shell is around 5 nm thick based on a mean diameter of 50 nm for the $Fe_3O_4$ core. The $Fe_3O_4$@Ag nanoparticles are aggregated together in FIG. 2, since the nanoparticles are magnetic at room temperature.

Figure 3:
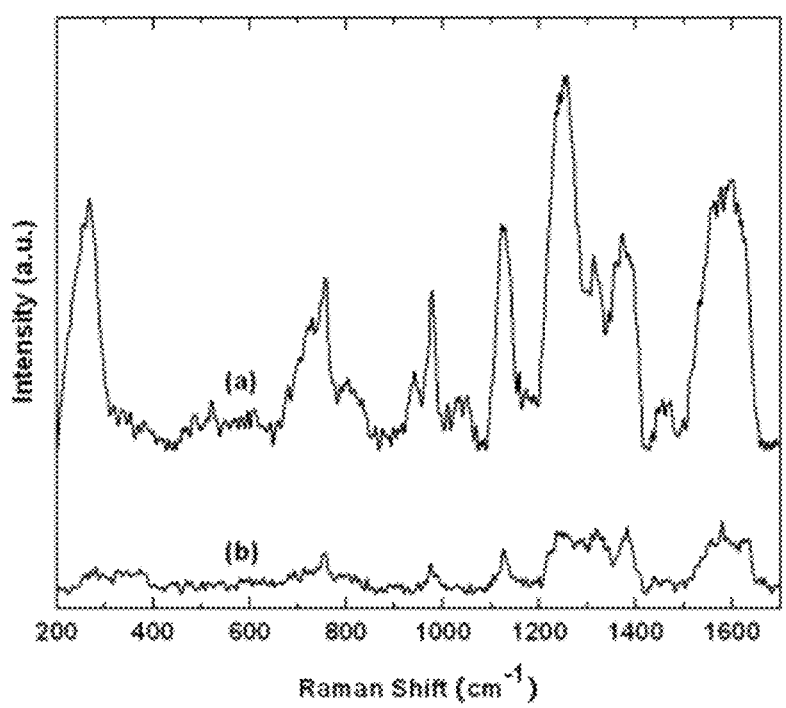
FIG. 3 shows (a) SERS spectrum of β-hematin in the close proximity of the SERS-active $Fe_3O_4$@Ag nanoparticles under the influence of a magnetic field and the excitation power was 20 mW; (b) Ordinary Raman spectrum of β-hematin and the excitation power was 2 mW in accordance with Example 1.

FIG. 3 gives (a) SERS Raman spectrum of β-hematin in the close proximity of the SERS-active $Fe_3O_4$@Ag nanoparticles under the influence of a magnetic field and (b) ordinary Raman spectrum of β-hematin. Raman peaks, such as 264 $cm^{-1}$, 753 $cm^{-1}$, 975 $cm^{-1}$, 1121 $cm^{-1}$, 1241 $cm^{-1}$, 1377 $cm^{-1}$, and 1623 $cm^{-1}$, can be observed in both the enhanced and ordinary Raman spectra of fabricated β-hematin, showing a degree of crystallinity comparable to those reported in the literature. In addition, the SERS spectrum of β-hematin are augmented by a few orders of magnitude compared with the ordinary Raman spectrum of β-hematin at the same concentration. The improvement in the Raman signal can be attributed to the electromagnetic and chemical enhancements between the $Fe_3O_4$@Ag nanoparticles and β-hematin in a close range under the influence of a magnetic field. The $Fe_3O_4$@Ag nanoparticles are therefore effective in enhancing the Raman signal of fabricated β-hematin crystals.

Example 2

SERRS and Magnetic Field-Enriched SERRS

In this example, the detection of β-hematin crystals using magnetic field-enriched SERRS enabled by $Fe_3O_4$@Ag nanoparticles was reported. This method enriches β-hematin crystals and $Fe_3O_4$@Ag nanoparticles by applying an external magnetic field and synergizes with the enhancement capability of SERRS, thereby promoting further augmentation in the Raman signal of β-hematin crystals. A parasitemia level of 10 parasites/μl in blood can be achieved by using this method in its current setup, which demonstrates the potential of employing magnetic field-enriched SERRS method in early malaria diagnosis.

Materials and Methods

Synthesis of β-Hematin

The β-hematin crystals were fabricated using an acid-catalyzed method (Egan et al., supra). A 0.1M NaOH solution dissolved with 7.9 mM of Ferriprotoporphyrin IX chloride [Cl—Fe(III)PPIX, hemin chloride, MP Biomedicals, USA] was heated inside a temperature bath of 60° C. and stirred at an estimated speed of 150 rpm. 1.45 ml of HCl (1 M) and 8.825 ml of acetate solution were added to the mixture, after 10 min and 14 min, respectively. The mixture was allowed to react for 46 min, prior to the removal of heat and left undisturbed in a dark environment for 24 hours. The solute was washed with methanol, deionized water, then filtered and collected with 0.2 μm supor filter for drying at room temperature over $P_2O_5$ for 48 h. The dry β-hematin powder was dissolved in 1N NaOH aqueous solution to obtain β-hematin solutions at concentrations ranging from $1\times10^{-2}$ M to $1\times10^{-9}$ M. NaOH was introduced to effectively disaggregate the large β-hematin pellet into smaller crystals by breaking the interchain hydrogen bonds between β-hematin molecules. Due to the low concentration of NaOH used, the conversion of β-hematin to hematin was insignificant as compared to other studies in which NaOH at a much higher concentration was used. This ensured that measured Raman spectra were mainly contributed by β-hematin, which is confirmed by the characteristic peaks of β-hematin present in the spectra. To investigate the magnetic enrichment effect in smaller β-hematin, precipitate was disposed and supernatant was collected for Raman measurements from a β-hematin suspension ($10^{-4}$ M) after centrifuging at 5000 rpm for 5 min (Sartorius 2-16, Sigma Laborzentrifugen, Germany).

Fabrication of $Fe_3O_4$@Ag Magnetic Nanoparticles

The seed-growth reduction method for fabricating iron oxide core and gold shell nanoparticles (Zhai et al., *J. Phys. Chem. C, "Fabrication of iron oxide core/gold shell submicrometer spheres with nanoscale surface roughness for efficient surface-enhanced Raman scattering"*, 2009, 113, (17), 7009-7014) was adapted to fabricate the present magnetic nanoparticles. First, a total of 16.2 mM $Fe_3O_4$ nanoparticles (Iron II, III oxide nanopowder, Sigma-Aldrich, USA) in ethanol (20 ml) was added dropwise to 80 ml of ethanol with 0.15 g of polyacrylic acid (Potassium polyacrylate, Sigma-Aldrich, USA). Then the mixture was placed in an ultrasonic bath (Elma E30H, Elma, Switzerland) for 15 min. The $Fe_3O_4$ nanoparticles were separated from the mixture using a magnet and washed with ethanol. The separated $Fe_3O_4$ nanoparticles were re-dispersed and diluted to 2.1 mM in a mixture of ethanol and deionized water (80.6:19.4% v/v) with a 2.8-mM $AgNO_3$ (Silver nitrate, Merck, USA) in the ultrasonic bath for 30 min. To reduce the silver salt, Triton X-100 (Triton X-100 Detergent, Bio-Rad Laboratories, USA), ethanol and deionized water (9.0:70.8:28.3% v/v/v) mixed with hydroxylamine hydrochloride (4.1 mM, Hydroxylamine hydrochloride, MP Biomedicals, USA) and NaOH (8.1 mM) was added dropwise (5.88 μl/sec) to the solution of $Fe_3O_4$ nanoparticles absorbed with $Ag^+$ salt. Finally, Triton X-100, ethanol and deionized water (2:65.3:32.7% v/v/v) with $AgNO_3$ (19.4 mM) was added dropwise (5.88 μl/sec) to the mixture. The mixture was washed and the $Fe_3O_4$@Ag magnetic nanoparticles were separated using a magnet. The resultant nanoparticles were suspended in 15 ml methanol and then filtered with 0.2 μm supor filters (0.2 μm supor syringe filters, Pall, USA).

Preparation of Analytes for Magnetic Field-Enriched SERRS Experiments

For the SERS measurements of R6G (Rhodamine 6G, Sigma-Aldrich, USA) absorbed on $Fe_3O_4$@Ag magnetic nanoparticles, R6G aqueous solutions were prepared at concentrations ranging from $10^{-6}$ to $10^{-9}$ M. A dried patch of magnetic nanoparticles was prepared by drying of 0.33 ml $Fe_3O_4$@Ag magnetic nanoparticles solution on a glass slide. The prepared R6G solution with volume of 0.33 ml was dropped onto the dried patch positioned inside an enclosed Petri dish to prevent concentration variation and evaporation. The substrate was rinsed to remove the excess R6G molecules and dried, prior to the SERS measurement.

As for the evaluation of SERRS measurements of the β-hematin crystals with and without magnetic field enrichment, the $Fe_3O_4$@Ag magnetic nanoparticles solution and β-hematin solution were placed under sonication (Elma E30H, Elma, Switzerland) each for 2 min. The two solutions were mixed together (1:1 v/v) and underwent sonication for another 2 min. In the SERRS and RRS experiments of the β-hematin crystals with and without magnetic field, the prepared β-hematin mixture (with $Fe_3O_4$@Ag nanoparticles in SERRS measurement) was dropped inside a small vial made with aluminum foil for measurements, since aluminum has been shown to give minimal background Raman signal within the spectral region of interest. The small vial was held under a magnetic field of 0.198 T and a magnetic field gradient of 26.6 T/m, during the SERRS and RRS measurements of β-hematin crystals with magnetic field-enrichment.

Field Emission Scanning Electron Microscope (FESEM) and Transmission Electron Microscope (TEM)

For taking FESEM images, a thin layer of platinum was coated (JEOL JFC-1600, JEOL, Japan) at 20 mA for 80 sec on the sample surface prior to the FESEM (JEOL JSM-6700F, JEOL, Japan) examination of $Fe_3O_4$@Ag magnetic nanoparticles and β-hematin crystals, with an accelerating voltage of 5 kV. In the TEM study, the TEM (JEOL 2010 TEM, JEOL, Japan) was operated at 200 kV to obtain the TEM images of the $Fe_3O_4$@Ag magnetic nanoparticles solution, which was dropped onto and dried on a copper TEM grid (copper TEM grid 300 mesh×83 μm pitch, Sigma-Aldrich, USA) prior to image acquisition.

Raman Instrumentation

The SERS signals of R6G were evaluated, and the SERRS and RRS properties of the β-hematin crystals with and without magnetic field were investigated using a micro-Raman spectrometer system (in Via, Renishaw, UK) coupled with a microscope (Alpha 300, WITec, Germany) in a backscattering geometry. A Czerny-Turner type spectrograph (f=250 mm) equipped with a holographic grating (1800 gr/mm) and a RamCam CCD detector (in Via, Renishaw, UK) were selected for all spectral measurements, which yields a spectral resolution of 2 $cm^{-1}$. A 633-nm laser (Renishaw, UK) beam was focused onto the samples on the substrates with a power of 10 mW and a spot size of about 3 μm through a microscope objective (20×, N.A. 0.4, Leica). All Raman spectra were collected with an exposure time of 15 seconds. Spectra measured from more than 5 different locations in each sample were averaged to improve the signal to noise ratio.

Results

Figure 4:
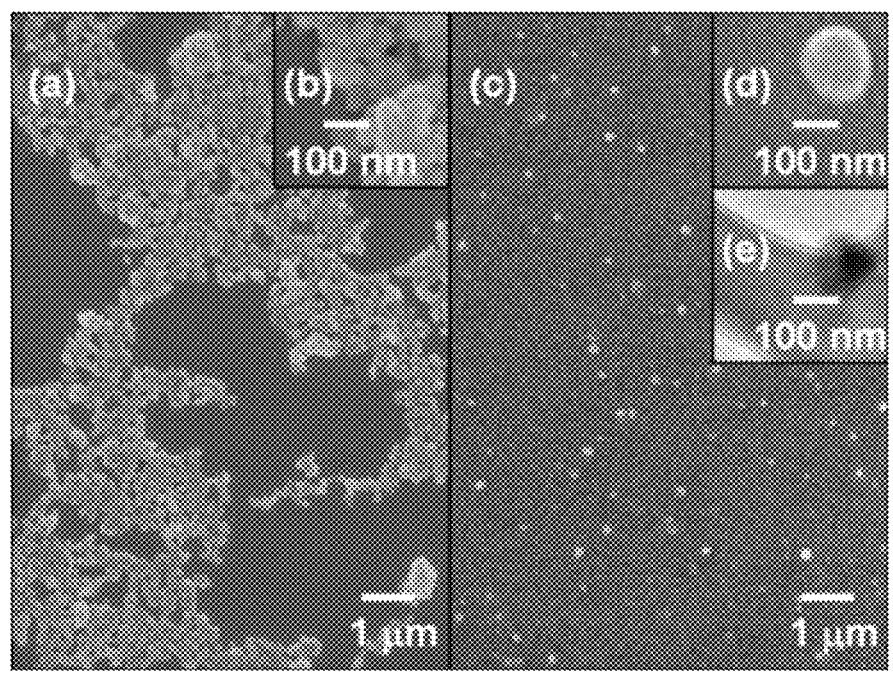
FIG. 4 shows (a) FESEM and (b) zoomed in FESEM image of raw $Fe_3O_4$ nanoparticles; (c) FESEM and (d) zoomed in FESEM image of $Fe_3O_4$@Ag nanoparticles; (e) TEM image of $Fe_3O_4$@Ag nanoparticles, in which $Fe_3O_4$ shows up as a darker core due to the higher electron density compare to the lighter Ag shell. Other structures in the image are attributed to Triton X-100 and methanol.

FIG. 4(*a*) gives the FESEM image of the raw $Fe_3O_4$ nanoparticles before coating with silver shell. The $Fe_3O_4$ nanoparticles have a mean diameter of 50 nm and they are aggregated together (FIG. 4(*b*)). To disaggregate the nanoparticles, polyacrylic acid (PAA) has been used for dispersing the nanoparticles as in the post-synthesis surface modification of $Fe_3O_4$ nanoparticles. Disaggregation of $Fe_3O_4$ nanoparticles prior to coating is important to ensure that each $Fe_3O_4$ nanoparticle would be uniformly coated with a silver shell. FIG. 4(*c*) shows the FESEM images of the $Fe_3O_4$ nanoparticles coated with silver shells. It can be clearly seen that the $Fe_3O_4$@Ag nanoparticles were well-dispersed. This dispersion was attributed to the use of triton X-100, which is known to be a surfactant used in Ag nanoparticles fabrication to prevent the nanoparticles from aggregating together. Each $Fe_3O_4$@Ag nanoparticle has a mean diameter of 150 nm (FIG. 4(*d*)) with an iron core whose diameter is 50 nm wrapped with a silver shell whose thickness is about 50 nm as shown by the TEM image (FIG. 4(*e*)). These well-dispersed $Fe_3O_4$@Ag nanoparticles are able to attach with β-hematin crystals more effectively thus leading to a stronger SERS enhancement compared to aggregated nanoparticles.

Figure 5:
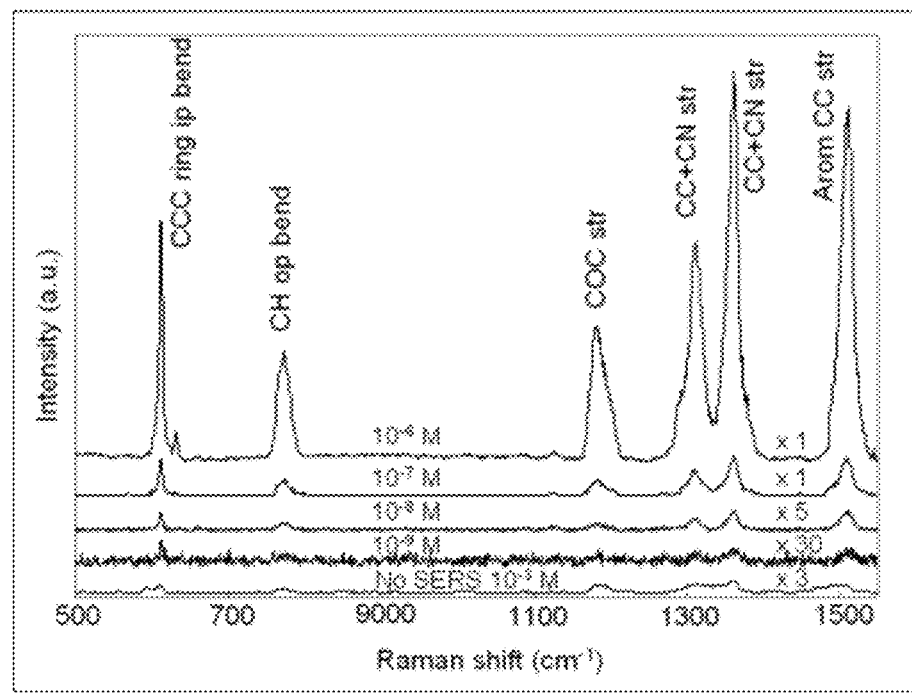
FIG. 5 shows SERS spectra of R6G at a range of concentrations ($10^{-6}$ to $10^{-9}$ M) adsorbed on $Fe_3O_4$@Ag nanoparticles compared to the ordinary Raman spectrum of R6G at a concentration of $10^{-3}$ M. The acronyms in the legends mean the following: ip: in-plane; op: out-off-plane; str: stretching; Arom: Aromatic.

FIG. 5 compares the SERS spectra of R6G at a range of concentrations varying from $10^{-6}$ M to $10^{-10}$ M adsorbed on the fabricated $Fe_3O_4$@Ag nanoparticles, with an ordinary Raman spectrum of R6G at a concentration of $10^{-3}$ M adsorbed on glass substrates. Most prominent Raman peaks, such as C—C—C ring in-plane bending (615 $cm^{-1}$), CH out-of-plane bending (775 $cm^{-1}$), C—O—C stretching (1185 $cm^{-1}$), C—C/C—N stretching (1310 $cm^{-1}$ and 1365

$cm^{-1}$), and aromatic C—C stretching (1508 $cm^{-1}$) can be observed in the SERS spectra of R6G. The minimum detectable concentration of R6G absorbed on the $Fe_3O_4$@Ag nanoparticles is $1\times10^{-9}$ M with a signal-to-noise ratio of 8 (S/N≈80/10).

In contrast, the peaks in the ordinary Raman spectrum of R6G adsorbed on the glass substrate without enhancement are not sharp even at a concentration of $10^{-3}$ M. It is estimated that the SERS enhancement factor (EF) of R6G adsorbed onto the $Fe_3O_4$@Ag nanoparticles relative to the ordinary Raman measurement ($EF_{SERS/Raman, R6G}$) was about $9.75\times10^6$, which is comparable to the EF values (around $10^6$ to $10^7$) of other isolated SERS active nanoparticles stated in the literature (Kneipp, K.; Kneipp, H.; Itzkan, I.; Dasari, R. R.; Field, M. S., "*Ultrasensitive chemical analysis by Raman spectroscopy*", Chem. Rev. 1999, 99, (10), 2957-2975), showing the feasibility of using the $Fe_3O_4$@Ag nanoparticles for enhancing the Raman signal of β-hematin crystals.

Figure 6:
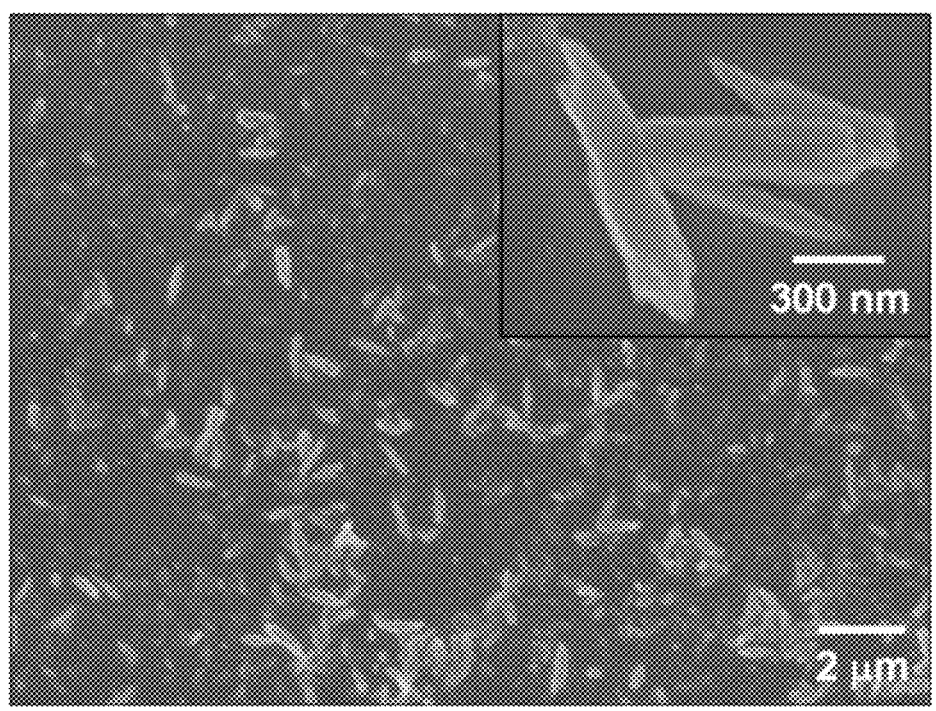
FIG. 6 shows a FESEM image of β-hematin crystals. The inset is the zoomed-in FESEM image of β-hematin crystals.

FIG. 6 shows the FESEM image of β-hematin crystals fabricated using the acid-catalyzed method described above. This method was employed because the fabricated β-hematin crystals, whose length was typically around 600 nm as shown in the inset of FIG. 6, is comparable in size to hemozoin biocrystals formed in the earlier malaria stage. This close resemblance in spatial dimensions between the two types of crystals would presumably result in similar SERRS enhancement. It should be noted that β-hematin crystals fabricated using the acid-catalyzed method may have low crystallinity. Thus, stronger SERRS enhancement than that shown in this example could be achieved for highly crystalline β-hematin or hemozoin crystals.

Figure 7:
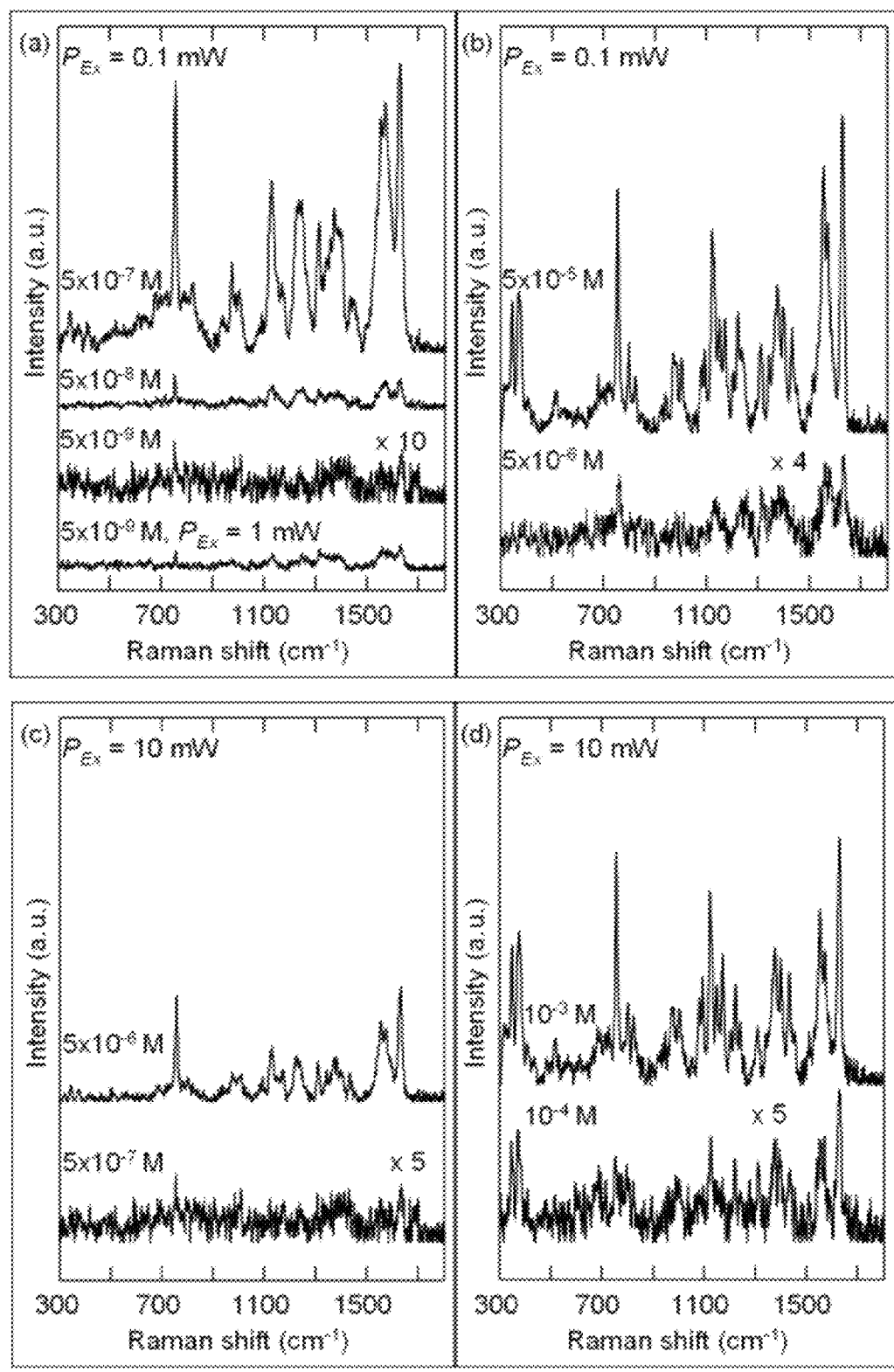
FIG. 7 shows (a) magnetic field-enriched SERRS spectra of β-hematin crystals at different concentrations. For the top three spectra, the excitation power $P_{Ex}$ was 0.1 mW and the concentration of β-hematin crystals was varied from κ×$10^{-7}$ M to 5×$10^{-9}$ M. For the bottom spectrum, the excitation power $P_{Ex}$ was 1 mW and the concentration was 5×$10^{-9}$ M; (b) SERRS spectra of β-hematin crystals at concentrations of 5×$10^{-5}$ M, and 5×$10^{-6}$ M at an excitation power of 0.1 mW; (c) magnetic field-enriched RRS spectra of β-hematin crystals at concentrations of 5×$10^{-6}$M, and 5×$10^{-7}$ M at an excitation power of 10 mW; (d) RRS spectra of β-hematin crystals at concentrations of $10^{-3}$ M, and $10^{-4}$ M at an excitation power of 10 mW. $P_{Ex}$ denotes Excitation power.

FIG. 7 compares spectra for the magnetic field-enriched SERRS, SERRS, magnetic field-enriched resonance Raman, and resonance Raman of β-hematin crystals at concentrations ranging from $10^{-3}$ M to $5\times10^{-9}$ M. Prominent vibrational features, such as $v_8$ (based on the electron spin and crystallographic coordination notation tetragonal $D_{4h}$ system for resonance Raman peaks studies on myoglobin) at 345 $cm^{-1}$, $\gamma_6$ at 367 $cm^{-1}$, $v_{15}$ at 754 $cm^{-1}$, $v_{22}$ at 1120 $cm^{-1}$, $v_{11}$ at 1551 $cm^{-1}$, $v_2$ at 1570 $cm^{-1}$, and $v_{10}$ at 1628 $cm^{-1}$, are noted in most of these spectra. The locations of these peaks are equal to those reported Raman peaks for hemozoin biocrystals (Frosch et al., 2007, supra.), confirming that the spectral features of β-hematin crystals are equivalent to hemozoin in Raman studies. It is clear that the effect of surface enhancement is dramatic when the RRS measurements (FIG. 7(d)) are compared with the SERRS (FIG. 7(b)). Moreover, high signal to noise ratios were observed in the magnetic field-enriched SERRS spectra of β-hematin crystals (FIG. 7(a)) even at low concentrations and small excitation power, compared to the SERRS (FIG. 7(b)), magnetic field-enriched RRS (FIG. 7(c)), and RRS (FIG. 7(d)) measurements.

Setting the smallest acceptable signal-to-noise ratio at 5 in the β-hematin spectra, the lowest detectable β-hematin concentrations for the magnetic field-enriched SERRS, SERRS, magnetic field-enriched RRS and RRS are $5\times10^{-9}$ M, $5\times10^{-6}$ M, $5\times10^{-7}$ M, and $5\times10^{-4}$ M, respectively, where the excitation power in the SERRS measurements was 0.1 mW and that in the RRS measurements was 10 mW.

It can be seen that magnetic field-enriched SERRS technique offers much higher enhancement in the Raman signal of the β-hematin crystals than SERRS alone by comparing FIGS. 7(a) and 7(b). To better understand the effect of magnetic field in the absence of nanoparticles, FIGS. 7(c) and 7(d) may be compared, in which magnetic field-enriched RRS shows a three orders of magnitude lower detectable concentration than RRS.

Discussion

It has been demonstrated the feasibility and significant improvement of magnetic field-enriched SERRS over traditional SERRS for detecting β-hematin crystals at very low concentrations. To gain additional insight into Raman enhancement in this technique, the enhancement factor (EF) in each of the following technique relative to the RRS measurement of β-hematin crystals was calculated: i) magnetic field-enriched SERRS ($EF_{magSERRS/RRS, β-hema}$), ii) SERRS without magnetic field ($EF_{SERRS/RRS, β-hema}$), and iii) magnetic field-enriched RRS ($EF_{magRRS/RRS, β-hema}$). These EFs were calculated by applying Eq. (1):

$$EF=(I_{1628, Augmented}/I_{1628, Ref})\times(N_{Ref}/N_{Augmented}) \quad \text{Eq. (1)}$$

where ($I_{1628, Augmented}/I_{1628, Ref}$), and ($N_{Augmented}/N_{Ref}$) are the ratio of Raman intensities at 1628 $cm^{-1}$, and the ratio of numbers of β-hematin molecules, respectively, in the measurements to be evaluated, i.e. magnetic field-enriched SERRS, SERRS, and magnetic field-enriched RRS, and the reference measurement, i.e. RRS. The estimated EF values are listed as follows: $EF_{magSERRS/RRS, β-hema}≈2.69\times10^7$, $EF_{SERRS/RRS, β-hema}≈3.60\times10^5$, and $EF_{magRRS/RRS, β-hema}≈68$.

Since $EF_{SERRS/RRS}$ is equivalent to $EF_{SERS/Raman}$ (Aoki, P. H. B.; Alessio, P.; Riul, A.; Saez, J. A. D. S.; Constantino, C. J. L., "*Coupling surface-enhanced resonance Raman scattering and electronic tongue as characterization tools to investigate biological membrane mimetic system*", Anal. Chem. 2010, 82, (9), 3537-3546), it is valid to make comparison between these two quantities and it is interesting to observe that the enhancement factor of SERRS relative to RRS for β-hematin ($EF_{SERRS/RRS, β-hema}≈3.60\times10^5$) was much smaller than that of SERS relative to ordinary Raman for R6G ($EF_{SERS/Raman, R6G}≈9.75\times10^6$). This observation could be attributed to the fact that the adsorption of β-hematin crystals onto $Fe_3O_4$@Ag nanoparticles is not as well as R6G molecules because of their rod shape and large size. Nevertheless, this reduced EF can be compensated by the magnetic field-enriched strategy (FIG. 7(a)).

The further augmentation due to the magnetic field-enriched effect in the SERRS and RRS measurements can be explained by the following effects induced by the external magnetic field. First, β-hematin crystals are enriched, which is similar to cell sorting and enrichment that have been reported previously (Kim, C. C.; Wilson, E. B.; DeRisi, J. L., "*Improved methods for magnetic purification of malaria parasites and haemozoin*", Malar. J. 2010, 9, (1), 17).

Second, the external magnetic field magnetizes β-hematin. Thus, the average distance between $Fe_3O_4$@Ag nanoparticles and β-hematin crystals was likely smaller, which resulted in stronger surface enhancement.

Finally, there was an increased number of $Fe_3O_4$@Ag nanoparticles available for binding to the β-hematin crystals due to the enriching effect of the external magnetic field. The potential mechanisms responsible for these effects may be elaborated as follows.

The enrichment of β-hematin crystals under an external magnetic field could be interpreted by using the conservation of momentum. Under an applied magnetic field, β-hematin crystals are magnetized since β-hematin crystal is paramagnetic. The magnetized crystals in a solution will typically form aggregates due to the attractive inter-crystal force between magnets. For each aggregate of β-hematin crystals in the experimental setup of this example, the magnetic force and the force of gravity are exerted in the direction of the magnetic field (downward direction), and counteracted by the viscous force. The present calculation based on Example 3 below shows that the aggregation of β-hematin crystals sinks much faster to the bottom of the vial under a magnetic field than individual crystals formed without the influence of a magnetic field. For example, the difference in the sinking speed can be as large as ten times for an aggregate of 25 crystals, which would result in a much faster enrichment of β-hematin crystals. The enrichment of β-hematin crystals allow the laser to excite more β-hematin crystals than the case of an individual β-hematin crystal, which was demonstrated by a value of 68 in $EF_{magRRS/RRS, \beta-hema}$ for RRS measurement under the influence of a magnetic field in the absence of nanoparticles (FIG. 7(c)). The enhancement in the magnetic field-enriched RRS (e.g. Raman peak at 1628 $cm^{-1}$ in FIG. 7(c)) is mainly attributed to the type A and B enhancement mechanisms reported previously (Wood, B. R.; Langford, S. J.; Cooke, B. M.; Lim, J.; Glenister, F. K; Duriske, M.; Unthank, J. K.; McNaughton, D., "*Resonance Raman spectroscopy reveals new insight into the electronics structure of β-hematin and malaria pigment*", *J. Am. Chem. Soc.* 2004, 126, (30), 9233-9239), arising from the transitions of excited electronic states. This process dominated over the aggregated enhanced Raman scattering of β-hematin crystals (e.g. Raman peak at 345 $cm^{-1}$ in FIG. 7(c)). The latter enhancement is related to the intermolecular interactions of aggregated molecules. These observations are seen in FIG. 7 as a higher intensity ratio of Raman peak at 1628 $cm^{-1}$ to 345 $cm^{-1}$ is noted for magnetic field enriched RRS ($\approx$8) than RRS ($\approx$2). Thus, a higher Raman signal of the β-hematin crystals can be achieved by the effect of magnetic field enrichment of β-hematin crystals in a solution.

The smaller interparticle distances and increased number of tightly-bounded aggregates formed between $Fe_3O_4@Ag$ nanoparticles and β-hematin crystals can be explained by employing the magnetic hetero-flocculation model. Since the $Fe_3O_4$ core of the nanoparticles is ferromagnetic, the magnetic field produced by each $Fe_3O_4@Ag$ nanoparticle would attract adjacent β-hematin crystals. The calculation based on Example 3 below illustrates that the attractive force between the $Fe_3O_4@Ag$ nanoparticles and β-hematin crystals is higher under an applied magnetic field, which suggests that more $Fe_3O_4@Ag$ nanoparticles are closer or tightly-bounded to β-hematin crystals, compared to the case without a magnetic field. This proposition is reconfirmed by FESEM images as in FIG. 8, which shows more $Fe_3O_4@Ag$ nanoparticles bounded to β-hematin crystals in a magnetic field (FIG. 8(a)) compared to the case without a magnetic field (FIG. 8(b)). The closer distance, denoted by d, between β-hematin crystals and $Fe_3O_4@Ag$ nanoparticles, can enhance electromagnetic field coupling in the SERS or SERRS phenomenon (FIG. 7(a)) because the enhancement is proportional to $1/d^3$. Furthermore, more $Fe_3O_4@Ag$ nanoparticles attached to the β-hematin crystals can also increase the SERS intensity (FIG. 7(a)), which are related to the number of analyte molecules attached to SERS nanoparticles.

All these three effects induced by the external magnetic field cause an improvement of around 74 times as noted in the $EF_{magSERRS/RRS, \beta-hema}$ (FIG. 7(a)) with reference to the $EF_{SERRS/RRS, \beta-hema}$ (FIG. 7(b)). Interestingly, the magnitude of improvement is similar to that in the RRS without the involvement of nanoparticles as in $EF_{magRRS/RRS, \beta-hema} \approx 68$. These results demonstrate that further Raman signal augmentation can be realized in the SERRS measurement of β-hematin crystals by taking advantage of the effect of magnetic field enrichment.

The detection sensitivity of β-hematin crystals by magnetic field-enriched SERRS could be converted or correlated to the concentration of malaria parasites in blood for practical evaluation. The detection limit of β-hematin concentration at $5 \times 10^{-9}$ M in the magnetic field-enriched SERRS measurement obtained in this example is equivalent to roughly 30 parasites/µl, considering a hemozoin concentration of about 0.22 pg/cell in the earlier malaria infection at the ring stage and hemozoin molecular weight of 1229 g/mol at the early stage (Serebrennikova, Y. M.; Patel, J.; Garcia-Rubio, L. H., "*Interpretation of ultraviolet-visible spectra of malaria parasite plasmodium falciparum*", *Appl. Opt.* 2010, 49, (2), 180-188).

In addition, this sensitivity is comparable to other rapid malaria detection techniques for hemozoin detection at later malaria stages, e.g. 10 parasites/µl (with hemozoin concentration at about 0.6 pg/cell) for laser desorption mass spectrometry and automated blood cell counters. Given that the laser excitation power used in this study was only 0.1 mW, the detection sensitivity of this new technique could be improved by at least one order of magnitude by increasing the excitation power to 1 mW. Several other aspects of the technique, such as the configuration of the magnetic field and the physical geometry of the SERS-active nanoparticles, could be optimized to further improve the detection sensitivity. With the high sensitivity magnetic field-enhanced SERRS, this technique has shown great potential for early malaria diagnosis.

Example 3

Enhancement Factor (EF) Calculation

In this example, the following EFs are calculated for the followings in accordance with Example 2.

For rhodamine 6G (R6G) molecules, the SERS EF of R6G molecules adsorbed onto the nanoparticles with iron oxide core and silver shell ($Fe_3O_4@Ag$) with respect to the ordinary Raman measurement ($EF_{SERS/Raman, R6G}$) has been calculated.

For β-hematin crystals, i) the magnetic field-enriched SERRS EF ($EF_{magSERRS/RRS}$), ii) the SERRS EF without magnetic field ($EF_{SERRS/RRS, \beta-hema}$) and iii) the magnetic field-enriched RRS EF ($EF_{magRRS/RRS, \beta-hema}$) relative to RRS measurements have been calculated. These EFs were calculated from Eq. (2) (Zhou, J.; Xu, S.; X, W.; Zhao, B.; Ozaki, Y., "*In situ nucleation and growth of silver nanoparticles in membrane materials: a controllable roughened SERS substrate with high reproducibility*", *J. Raman Spectrosc.* 2009, 40, (1), 31-37), $$EF = \frac{I_{\Delta, Augmented}}{I_{\Delta, Ref}} \times \frac{P_{Augmented}}{P_{Ref}} \times \frac{N_{Ref}}{N_{Augmented}} \qquad \text{Eq. (2)}$$

where ($I_{\Delta, Augmented}/I_{\Delta, Ref}$), ($P_{Augmented}/P_{Ref}$) and ($N_{Augmented}/N_{Ref}$) are the ratios of the Raman intensities at Raman shift of 4, excitation powers, and numbers of analyte molecules in enhanced and referenced measurements. The details of each EF calculation are given below.

Calculation of $EF_{SERS/Raman, R6G}$

In the calculation of $EF_{SERS/Raman, R6G}$, the expression for $N_{Augmented}$ is different from Zhou et al., 2009 (supra.), since the $Fe_3O_4@Ag$ nanoparticles are different from a continuous film. The number of R6G molecules adsorbed in the focused area can be estimated by, $N_{SERS,\ R6G} \times A_{LS}/A_{Cast} = 1.28 \times 10^5$, where $N_{SERS,\ R6G}$ is the number of R6G molecules at a concentration of $1 \times 10^{-6}$ M in a volume ($V_{size}$) of 0.33 μl, $A_{LS}$ is the laser spot area ($\approx 1.26 \times 10^{-11}$ m$^2$), and $A_{Cast}$ is the area of dried $Fe_3O_4@Ag$ nanoparticles ($\approx 1.96 \times 10^{-5}$ m$^2$). The area of nanoparticles is larger than the laser spot area so only those nanoparticles within the laser spot contribute to measured signals. The calculation avoids the over-estimation of the number of R6G molecules, using expression adopted from Zhou et al., 2009 (supra.), $A_{LS} \times 4\pi r^2 \times \rho_{population}/A = 4.88 \times 10^5$, where r is the mean radius of a $Fe_3O_4@Ag$ nanoparticle 75 nm), n population is the density of $Fe_3O_4@Ag$ nanoparticles ($\approx 7.13 \times 10^{11}$ m$^2$), and A is the occupied average area for one R6G molecule (130 Å$^2$).

Therefore, the $EF_{SERS/Raman,\ R6G}$ can be calculated as, $$EF = \frac{I_{1365,Augmented}}{I_{1365,Ref}} \times \frac{P_{Augmented}}{P_{Ref}} \times \frac{N_{Ref}}{N_{Augmented}}$$

$$= \frac{I_{1365,Augmented}}{I_{1365,Ref}} \times \frac{P_{Augmented}}{P_{Ref}} \times \frac{Conc_{Ref} \times V_{size} \times L \times (A_{LS}/A_{Cast})}{Conc_{Augmented} \times V_{size} \times L \times (A_{LS}/A_{Cast})}$$

$$= \frac{44026}{452} \times \frac{10\ mW}{0.1\ mW} \times \frac{10^{-3}\ M}{10^{-6}\ M}$$

$$\approx 9.75 \times 10^6$$

where the two numbers 44026 and 452 are the SERS and ordinary Raman intensities of R6G adsorbed on $Fe_3O_4@Ag$ nanoparticles, respectively, at the concentrations of $10^{-6}$ M and $10^{-3}$ M (as in FIG. 5 in Example 2), and L is the Avogadro's number.

Calculation of $EF_{MagSERRS/RRS,\ hema}$

Figure 8:
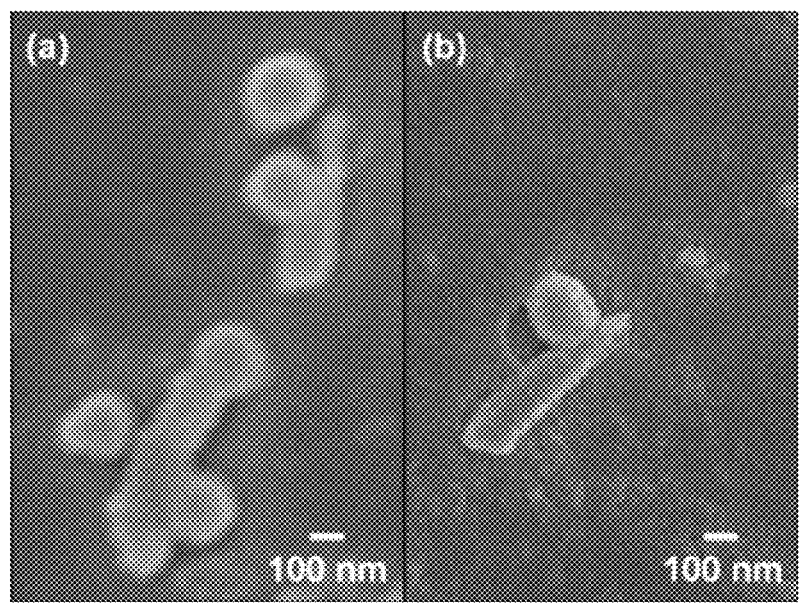
FIG. 8 shows FESEM images of $Fe_3O_4$@Ag nanoparticles and β-hematin crystals (a) with and (b) without the external magnetic field.

For the calculation of $EF_{magSERRS/RRS,\ hema}$ of β-hematin crystals in magnetic field-enriched SERRS, it is assumed that the SERRS intensities are mainly contributed by the clusters that involve one β-hematin molecule in close vicinity to two $Fe_3O_4@Ag$ nanoparticles as shown in FIG. 8 of Example 2. Since SERS effect is significant only for the test molecules within a distance of about 35 nm from SERS nanoparticles (Lee, S. J.; Guan, Z.; Xu, H.; Moskovits, M., "Surface-enhanced Raman spectroscopy and nanogeometry: The plasmonic origin of SERS", J. Phys. Chem. C 2007, 111, (49), 17985-18988), it is assumed that the effective SERS area in a β-hematin crystal resembles two hemispheres next to nanoparticles, whose radii ($r_{SERS,\ rad}$) are around 35 nm. Each β-hematin crystal occupies a volume ($V_{hema}$) of roughly $2.1 \times 10^{-20}$ m$^3$.

Therefore, the $EF_{magSERRS/RRS}$ can be determined by, $$EF = \frac{I_{1628,Augmented}}{I_{1628,Ref}} \times \frac{P_{Augmented}}{P_{Ref}} \times \frac{N_{Ref}}{N_{Augmented}}$$

$$= \frac{I_{1365,Augmented}}{I_{1365,Ref}} \times \frac{P_{Augmented}}{P_{Ref}} \times$$

$$\frac{Conc_{Ref} \times V_{size} \times L \times (A_{LS}/A_{Cast})}{Conc_{Augmented} \times V_{size} \times L \times (A_{LS}/A_{Cast}) \times \left(\frac{4}{3}\pi r^3_{SERS,rad}/V_{hema}\right)}$$

$$= \frac{1494}{1300} \times \frac{10\ mW}{0.1\ mW} \times \frac{10^{-3}\ M}{5 \times 10^{-7}\ M} \times \frac{2.1 \times 10^{-20}\ m^3}{(4/3)\pi(r_{SERS,rad})^3\ m^3}$$

$$\approx 2.57 \times 10^7$$

where 1494 and 1300 are the intensities of the magnetic field-enriched SERRS and RRS of β-hematin crystals, respectively, at the concentrations of $5 \times 10^{-7}$ M and $10^{-3}$ M (FIGS. 7(a) and 7(d) in Example 2).

Calculation of $EF_{SERRS/RRS,\ hema}$

In the calculation of $EF_{SERRS/RRS,\ hema}$ of β-hematin crystals in SERRS without any magnetic field, it is assumed that only one $Fe_3O_4@Ag$ nanoparticle is in close vicinity to each β-hematin crystals (FIG. 8 of Example 2), thus contributing to SERRS on average.

Thus, the $EF_{SERRS/RRS,\ hema}$ can be calculated by, $$EF = \frac{I_{1365,Augmented}}{I_{1365,Ref}} \times \frac{P_{Augmented}}{P_{Ref}} \times \frac{N_{Ref}}{N_{Augmented}}$$

$$= \frac{I_{1365,Augmented}}{I_{1365,Ref}} \times \frac{P_{Augmented}}{P_{Ref}} \times$$

$$\frac{Conc_{Ref} \times V_{size} \times L \times (A_{LS}/A_{Cast})}{Conc_{Augmented} \times V_{size} \times L \times (A_{LS}/A_{Cast}) \times \left(\frac{2}{3}\pi r^3_{SERS,rad}/V_{hema}\right)}$$

$$= \frac{100}{1300} \times \frac{10\ mW}{0.1\ mW} \times \frac{10^{-3}\ M}{5 \times 10^{-6}\ M} \times \frac{2.1 \times 10^{-20}\ m^3}{(2/3)\pi(r_{SERS,rad})^3\ m^3}$$

$$\approx 3.60 \times 10^5$$

where 100 and 1300 are the SERRS and RRS intensities of β-hematin crystals, respectively, at the concentrations of $5 \times 10^{-6}$ M and $10^{-3}$ M (FIGS. 7(b) and 7(d) in Example 2).

Calculation of $EF_{MagRRS/RRS,\ hema}$

For the calculation of $EF_{magRRS/RRS,\ hema}$ of β-hematin crystals in the magnetic field-enriched RRS, β-hematin crystals are assumed to be evenly distributed in the laser spot area.

Therefore, $EF_{MagRRS/RRS,\ hema}$ can be calculated by, $$EF = \frac{I_{1365,Augmented}}{I_{1365,Ref}} \times \frac{P_{Augmented}}{P_{Ref}} \times \frac{N_{Ref}}{N_{Augmented}}$$

$$= \frac{442}{1300} \times \frac{100\ mW}{100\ mW} \times \frac{10^{-3}\ M}{5 \times 10^{-6}\ M}$$

$$= 68$$

where 442 and 1300 are the magnetic field-enriched RRS and RRS intensities of the β-hematin crystals, respectively, at the concentrations of $5 \times 10^{-6}$ M and $10^{-3}$ M (FIGS. 7(c) and 7(d) in Example 2).

β-Hematin Crystal Velocity Calculation

Figure 9:
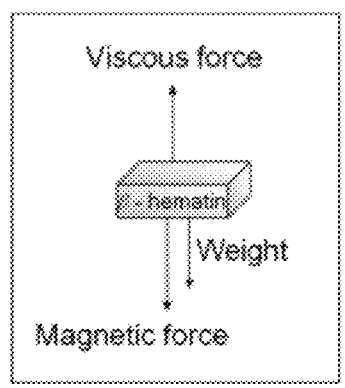
FIG. 9 shows forces exerted onto a β-hematin crystal in a magnetic field in accordance with Example 3.

FIG. 9 gives the forces exerted on a β-hematin crystal (with an equivalent radius, $r_{hema}$, of about $1.7 \times 10^{-7}$ m for a sphere with a volume of $V_{hema}$) under a magnetic flux (B=0.2 T) at a magnetic flux gradient (dB/dx=26.6 T·m$^{-1}$). Under equilibrium, the magnetic force ($F_m$), the weight ($F_w$), and the counteracting viscous force ($F_v$), can be expressed as Eq. (3) (Holligan, D. L.; Gillies, G. T; Dailey, J. P., "Magnetic guidance of ferrofluidic nanoparticles in an in vitro model of intraocular retinal repair", Nanotechnology 2003, 14, (6), 661-666), $$F_m + F_w = F_v \quad \text{Eq. (3)}$$

Expanding the expression for each force yields, $$\chi_{hema}\frac{V_{hema}B}{\mu_0}(dB/dx) + V_{hema}\rho_{hema}g = 6\pi\eta r_{hema}v \qquad \text{Eq. (4)}$$

Where $\rho_{hema}$ is the density of β-hematin (1.45 g·m$^{-3}$) (Pagola, S.; Stephens, P. W.; Bohle, D. S.; Kosar, A. D.; Madsen, S. K., "*The structure of malaria pigment β-haematin*", Nature 2000, 404, (6775), 307-310), g is acceleration of gravity, $\chi_{hema}$ is the magnetic susceptibility of β-hematin (13.65×10$^{-3}$ emu/mol) (Bohle, D. S.; Conklin, B. J.; Cox, D.; Madsen, S. K.; Paulson, S.; Stephens, P. W; Yee, G. T, "*Structural and spectroscopic studies of β-hematin (the heme coordination polymer in malaria pigment)*", ACS Symp. Ser. 1994, 572, 497-515), $\mu_0$ is the magnetic permeability of vacuum, η is the viscosity of water (890 μN·s·m$^{-2}$) (Holligan, 2003, supra.) and v is the velocity of the β-hematin crystal. According to Eq. (4), an order of magnitude increment is noted in the velocity (sinking downward) for an aggregate of 25 β-hematin crystals (≈1 μm·sec$^{-1}$) under a magnetic field compared to a single β-hematin crystal in an environment without magnetic field (≈0.1 μm·sec$^{-1}$).

Figure 10:
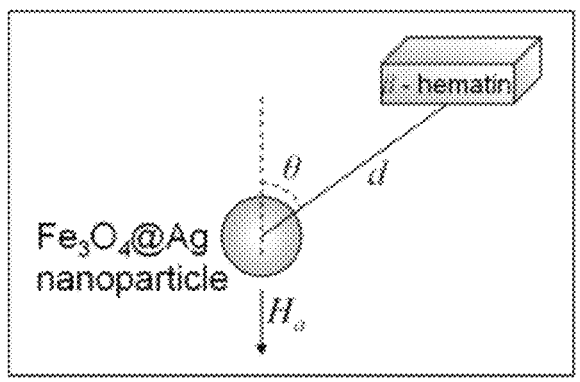
FIG. 10 shows a β-hematin crystal and a $Fe_3O_4$@Ag nanoparticle in an applied magnetic field in accordance with Example 3.
Figure 11:
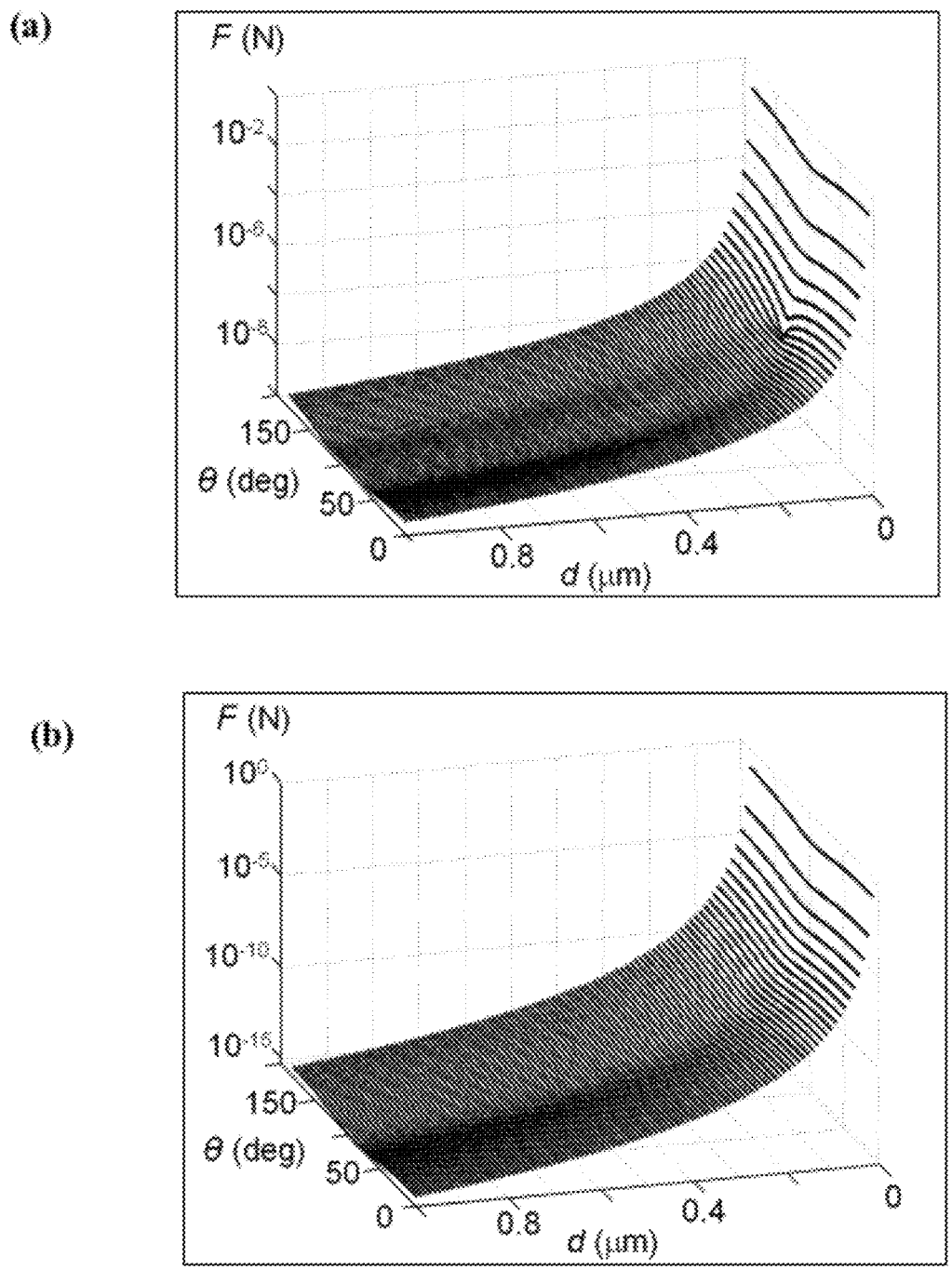
FIG. 11 shows the dependence of magnetic force (F) variation on the distance (d) between a β-hematin crystal and a $Fe_3O_4$@Ag nanoparticle, (a) in an applied magnetic field, and (b) without a magnetic field in accordance with Example 3.

Magnetic Force Calculation Between a Fe$_3$O$_4$@Ag Nanoparticle and a β-Hematin Crystal FIG. 10 shows a β-hematin crystal and a Fe$_3$O$_4$@Ag nanoparticle in the applied magnetic field ($H_a$=B/$\mu_0$), positioned on an axis (a line joining the centers of the β-hematin crystal and the Fe$_3$O$_4$@Ag nanoparticle at a distance, d, apart) at an angle θ relative to the magnetic field direction. The β-hematin crystal is approximated to be a sphere with volume equivalent to $V_{hema}$ and the Fe$_3$O$_4$@Ag nanoparticle is assumed to be a Fe$_3$O$_4$ nanoparticle with a radius of 25 nm. Thus, the attractive force between the β-hematin crystal and the Fe3O4@Ag nanoparticle in the radial ($F_r$, parallel to the axis) and angular ($F_\theta$, perpendicular to the axis) directions can be expressed as Eq. (5) and (6), based on a previous model (Ebner, A. D.; Ploehn, H. J.; Ritter, J. A., "*Magnetic field orientation and spatial effects on the retention of paramagnetic nanoparticles with magnetite*", Sep. Purif. Technol. 2002, 37, (16), 3727-3753):

$$F_r = -V_{hema}\mu_0(\chi_{hema}-\chi) \qquad \text{Eq. (5)}$$
$$\left(\frac{r^3M}{d^4}\right)\left[2\left(H_a + \frac{2r^3}{3d^3}M\right)\cos^2\theta + \left(-H_a + \frac{r^3}{3d^3}M\right)\sin^2\theta\right]$$

$$F_\theta = -V_{hema}\mu_0(\chi_{hema}-\chi) \qquad (6)$$
$$\left[-\left(H_a + \frac{2r^3}{3d^3}M\right)^2 + \left(-H_a + \frac{r^3}{3d^3}M\right)^2\right]\frac{\cos\theta\sin\theta}{d},$$

Where χ is the magnetic susceptibility (3 SI) and M is the saturation magnetization of Fe$_3$O$_4$ (65.4 emu/g) (Goya, G. F.; Berquo, T S.; Fonseca, F. C.; Morales, M P., "*Static and dynamic magnetic properties of spherical magnetite nanoparticles*", J. Appl. Phys. 2003, 94, (5), 3520-3528; Heider, F.; Zitelsberger, A.; Fabian, K, "*Magnetic susceptibility and remanent coercive force in grown magnetite crystals from 0.1 μm to 6 mm*", Phys. Earth Planet In. 1996, 93, (3-4), 239-256). FIG. 11 illustrates the magnetic force, $F=[(F_r)^2+(F_\theta^2)]^{0.5}$, for d ranging from 10 nm to 1 nm, showing the stronger magnetic force in the applied magnetic field (FIG. 11(a)) than without the applied field (FIG. 11(b)).

Example 4

SERRS and Magnetic Field-Enriched SERRS

In this example, the detection of β-hematin crystals using magnetic field-enriched SERRS enabled by Fe$_3$O$_4$@Ag nanoparticles was optimised and reported. This method enriches β-hematin crystals and Fe$_3$O$_4$@Ag nanoparticles by applying an external magnetic field and synergizes with the enhancement capability of SERRS, thereby promoting further augmentation in the Raman signal of β-hematin crystals. The magnetic field-enriched SERRS signal of β-hematin crystals shows approximately five orders of magnitude enhancement in the resonance Raman signal, in comparison to about three orders of magnitude improvement in the SERRS signal without the influence of magnetic field. The improvement has led to a β-hematin detection limit at a concentration of 5 nM (roughly equivalent to 30 parasites/μl at the early stages of malaria infection), which demonstrates the potential of magnetic field-enriched SERRS technique in early malaria diagnosis.

Materials and Methods

Fabrication of Fe3O4@Ag Magnetic Nanoparticles

We synthesized the nanoparticles with iron oxide core and silver shell by using the seed-growth reduction method (Zhai et al., 2009, supra.). First, a total of 16.2 mM Fe3O4 nanoparticles (Iron II, III oxide nanopowder, Sigma-Aldrich, USA) in ethanol (20 ml) was added drop-wise to 80 ml of ethanol with 0.15 g of polyacrylic acid (Potassium polyacrylate, Sigma-Aldrich, USA). Then the mixture was sonicated (Elma E30H, Elma, Switzerland) for 15 min. The Fe3O4 nanoparticles were separated with a magnet and washed with ethanol. The separated Fe3O4 nanoparticles were re-dispersed (2.1 mM) in a mixture of ethanol and deionized water (80.6:19.4% v/v) with a 2.8 mM AgNO3 (Silver nitrate, Merck, USA) in the ultrasonic bath for 30 min. To reduce the silver salt, Triton X-100 (Triton X-100 Detergent, Bio-Rad Laboratories, USA), ethanol and deionized water (9.0:70.8:28.3% v/v/v) mixed with hydroxylamine hydrochloride (4.1 mM, MP Biomedicals, USA) and NaOH (8.1 mM) was added drop-wise (5.88 μl/s) to the suspension of Fe3O4 nanoparticles absorbed with Ag$^+$ salt. Finally, Triton X-100, ethanol and deionized water (2:65.3:32.7% v/v/v) with AgNO$_3$ (19.4 mM) was added drop-wise (5.88 μl/s) to the mixture. The mixture was washed and the Fe3O4@Ag magnetic nanoparticles were separated using a magnet. The resulting nanoparticles were suspended in 15 ml methanol and then filtered with 0.2 μm supor filters (0.2 μm supor syringe filters, Pall, USA).

Synthesis of β-Hematin Crystals

β-hematin crystals were fabricated using an acid-catalyzed method (Egan, 2001, supra.). A 0.1 M NaOH solution dissolved with 7.9 mM of Ferriprotoporphyrin IX chloride [Cl—Fe(III)PPIX, hemin chloride, MP Biomedicals, USA] was heated at 60° C. and stirred at 150 rpm. 1.45 ml of HCl (1 M) and 8.825 ml of acetate solution were added to the mixture, after 10 min and 14 min, respectively. After another 46 min, the heater was removed and the mixture was left undisturbed in a dark environment for 24 h. The solute was washed with methanol and deionized water sequentially, then filtered and collected with 0.2 nm supor filter for drying at room temperature over P2O5 for 48 h. The dry β-hematin powder was resuspended by aqueous NaOH at concentrations ranging from 10$^{-4}$ M to 10$^{-11}$ M to obtain β-hematin suspension at concentrations ranging from 1×10$^{-2}$ M to 1×10$^{-9}$ M. NaOH was introduced to effectively disaggregate the large β-hematin pellet into smaller crystals by breaking the interchain hydrogen bonds between β-hematin molecules. Due to the low concentration of NaOH used, the conversion of β-hematin to hematin was insignificant as compared to other studies in which NaOH at a much higher concentration was used. This ensured that measured Raman spectra were mainly contributed by β-hematin, which is confirmed by the characteristic peaks of β-hematin present in the spectra. To investigate the magnetic enrichment effect in smaller β-hematin, precipitate was disposed and supernatant was collected for Raman measurements from a β-hematin suspension ($10^{-4}$ M) after centrifuging at 5000 rpm for 5 min (Sartorius 2-16, Sigma Laborzentrifugen, Germany).

Preparation of Analytes for Magnetic Field-Enriched SERRS Experiments

For the SERS measurements of R6G (Rhodamine 6G, Sigma-Aldrich, USA) absorbed on Fe3O4@Ag magnetic nanoparticles, R6G aqueous solutions were prepared at concentrations ranging from $10^{-6}$ to $10^{-8}$ M. As for the evaluation of SERRS measurements of β-hematin crystals with and without magnetic field enrichment, the suspension of Fe3O4@Ag magnetic nanoparticles and β-hematin solution were each sonicated for 2 min. They were then mixed together (1:1 v/v) and underwent sonication for another 2 min. In all Raman measurements, the analyte was dropped inside a small vial made with aluminum foil for measurements, since aluminum has shown to give minimal background Raman signal within the spectral region of interest in this study. The small vial was placed on top of a magnet, around which the magnetic field was 0.198 T and the magnetic field gradient was 26.6 T/m, during the SERRS and RRS measurements with magnetic field enrichment.

Field Emission Scanning Electron Microscope and Transmission Electron Microscope with Energy-Dispersive X-Rays Analysis For taking field emission scanning electron microscope (FESEM) images, a thin layer of platinum was coated with a fine coater (JEOL JFC-1600, JEOL, Japan) at 20 mA for 80 s on the sample surface prior to the FESEM (JEOL JSM-6700F, JEOL, Japan) examination of Fe3O4@Ag magnetic nanoparticles and β-hematin, with an accelerating voltage of 5 kV. In the transmission electron microscope (TEM) study, the TEM (JEOL 2100F TEM, JEOL, Japan) equipped with an energy-dispersive X-ray (EDX) analyzer was operated at 200 kV to obtain the TEM images and corresponding EDX of the Fe3O4@Ag magnetic nanoparticles. The sample was prepared by drying nanoparticle suspension that was dropped onto a copper TEM grid (300 mesh holey-carbon copper TEM grid, Ted Pella, USA) prior to image acquisition.

Raman Instrumentation

The SERS signals of R6G, were evaluated and the SERRS and RRS properties of β-hematin crystals with and without magnetic field were investigated using a micro-Raman spectrometer system (in Via, Renishaw, UK) coupled with a microscope (Alpha 300, WITec, Germany) in a backscattering geometry. A Czerny-Turner type spectrograph (f ¼ 250 mm) equipped with a holographic grating (1800 gr/mm) and a RemCam CCD detector (in Via, Renishaw, UK) were selected for all spectral measurements, which yields a spectral resolution of 2 $cm^{-1}$. A 633 nm laser (Renishaw, UK) beam, reported to be feasible for inducing SERS effect on Ag, was focused onto the samples at a spot size of about 3 μm through a microscope objective (20×, N.A. 0.4, Leica). The excitation power was 0.1 mW for all SERS and SERRS measurement, which is typically used in literature to avoid localized heating, and 10 mW for the ordinary Raman experiment. A signal-to-noise ratio, S/N, of about 5 was required in all Raman spectra for the determination of minimum detectable concentrations of R6G and β-hematin, where N was the average noise intensity in the spectral region next to a representative Raman peak (1000 $cm^{-1}$ for R6G and at 1750 $cm^{-1}$ for β-hematin), and S was the difference between the peak intensity (1635 $cm^{-1}$ for R6G and 1628 $cm^{-1}$ for β-hematin) and the average noise intensity. All Raman spectra were collected with an exposure time of 15 s, and averaged from more than five different locations with a standard deviation of less than 5% for R6G, and of less than 10% for β-hematin. In each raw spectrum, a fifth-order polynomial was found to be optimal for fitting the fluorescence background, in which this polynomial was subtracted from the raw spectrum to yield the final spectrum.

Results

Figure 12:
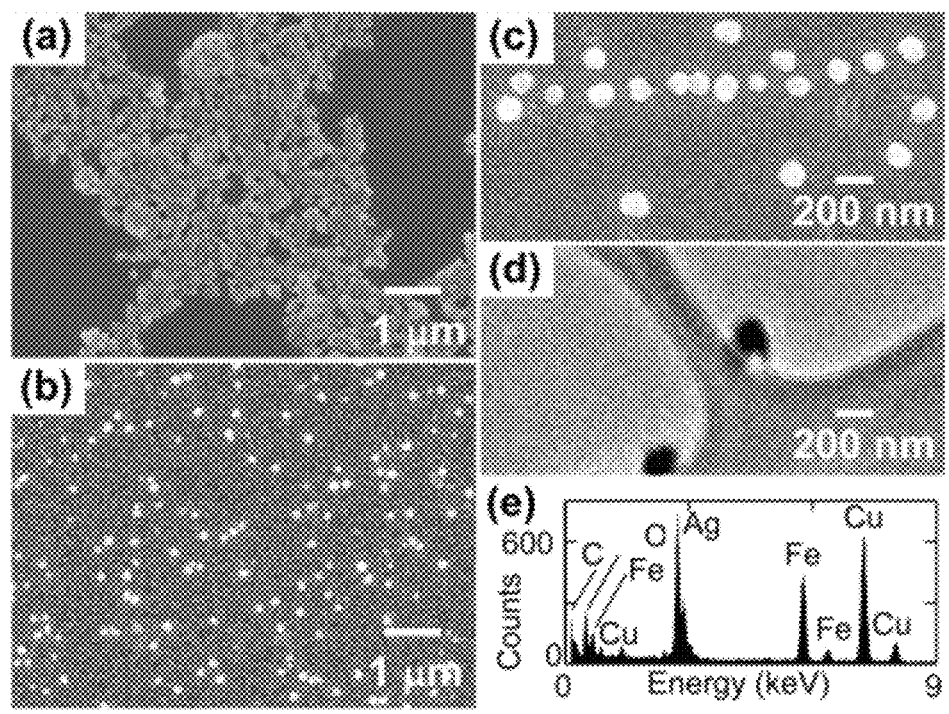
FIG. 12 shows (a) FESEM image of raw $Fe_3O_4$ nanoparticles; (b) FESEM and (c) zoomed in FESEM image of Ag nanoparticles; (d) Representative TEM image of $Fe_3O_4$@Ag nanoparticles of Example 4 (Other structures in the image are attributed to surfactant) 1; (e) EDX of the $Fe_3O_4$@Ag nanoparticles.
Figure 13:
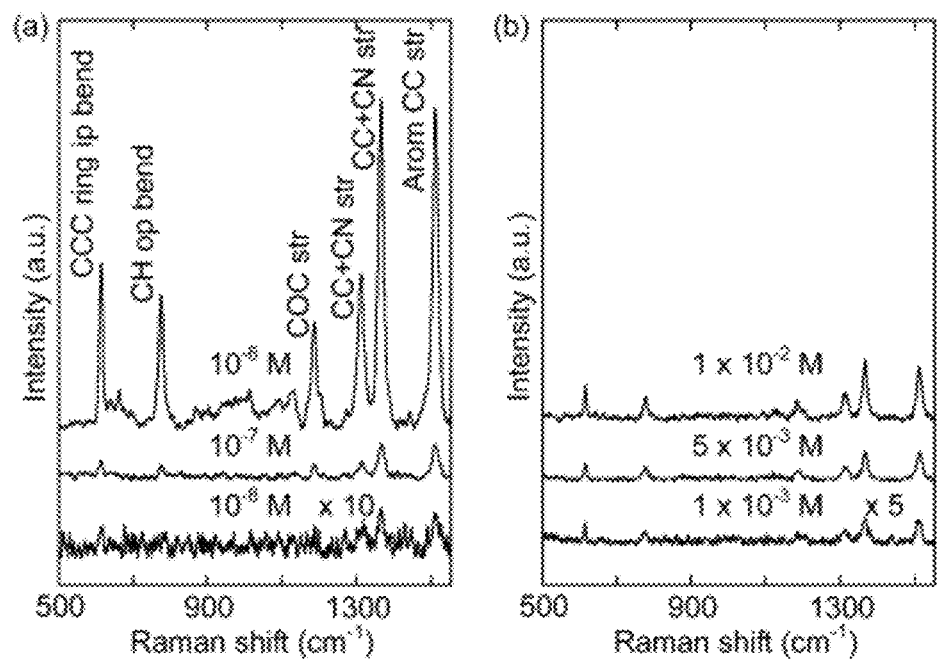
FIG. 13 shows (a) SERS spectra of R6G solution at concentrations of $10^6$ M, $10^{-7}$ M, and $10^{-8}$ M, with $Fe_3O_4$@Ag nanoparticles, at laser excitation power of 0.1 mW. (b) Ordinary Raman spectra of R6G at concentrations of 1×$10^{-2}$ M, 5×$10^{-3}$ M, and 1×$10^{-3}$ M, at laser excitation power of 10 mW. The acronyms in the legends mean the following. ip: inplane; op: out-off-plane; str: stretching; Arom: Aromatic.

FIG. 12(a) gives the FESEM image of the raw Fe3O4 nanoparticles. Individual Fe3O4 nanoparticles have a mean diameter of about 50 nm (±5 nm). FIG. 12(b) shows the FESEM images of the Fe3O4 nanoparticles coated with silver shells. The Fe3O4@Ag nanoparticles were well dispersed in the image. Each Fe3O4@Ag nanoparticle has a mean diameter of about 140 nm (FIG. 12(c)), with a size range±20 nm characterized by zetasizer measurements. The core-shell geometry is reconfirmed by the TEM image [FIG. 12(d)] with an EDX spectrum [FIG. 12(e)] that reveals the elemental composition of the nanoparticle. Fe, Ag, O, Cu and C can be observed in the EDX graph. Fe, O and Ag signals are originated from the Fe3O4 core and Ag shell, while Cu, and C are attributed to the copper grid. FIG. 13 compares the SERS spectra of aqueous R6G solution adsorbed on the fabricated Fe3O4@Ag nanoparticles [FIG. 13(a), concentrations varying from $10^{-6}$ M to $10^{-8}$ M] with the ordinary Raman spectra of R6G solution [FIG. 13(b), concentrations varying from $10^{-2}$ M to $10^{-3}$ M]. Most prominent Raman peaks, such as C—C—C ring in-plane bending (615 $cm^{-1}$), CH out-of-plane bending (775 $cm^{-1}$), C—O—C stretching (1185 $cm^{-1}$), C—C/C—N stretching (1310 $cm^{-1}$ and 1365 $cm^{-1}$), and aromatic C—C stretching (1508 $cm^{-1}$), can be observed in the SERS spectra of R6G. The minimum detectable concentration of R6G absorbed on the Fe3O4@Ag nanoparticles is $1 \times 10^{-8}$ M, which is five orders of magnitude more sensitive than that of $10^{-3}$ M detected in the ordinary Raman spectrum without enhancement. It is estimated that the analytical enhancement factor (AEF) of the SERS signals relative to the ordinary Raman measurement (AEFSERS/Raman; R6G) is about $5.77 \times 10^6$, which is comparable to the AEF values (around $10^3$ to $10^6$) of nanoparticle colloids stated in the literature. These results suggested the feasibility of using the Fe3O4@Ag nanoparticles for enhancing the Raman signal of β-hematin crystals.

Figure 14:
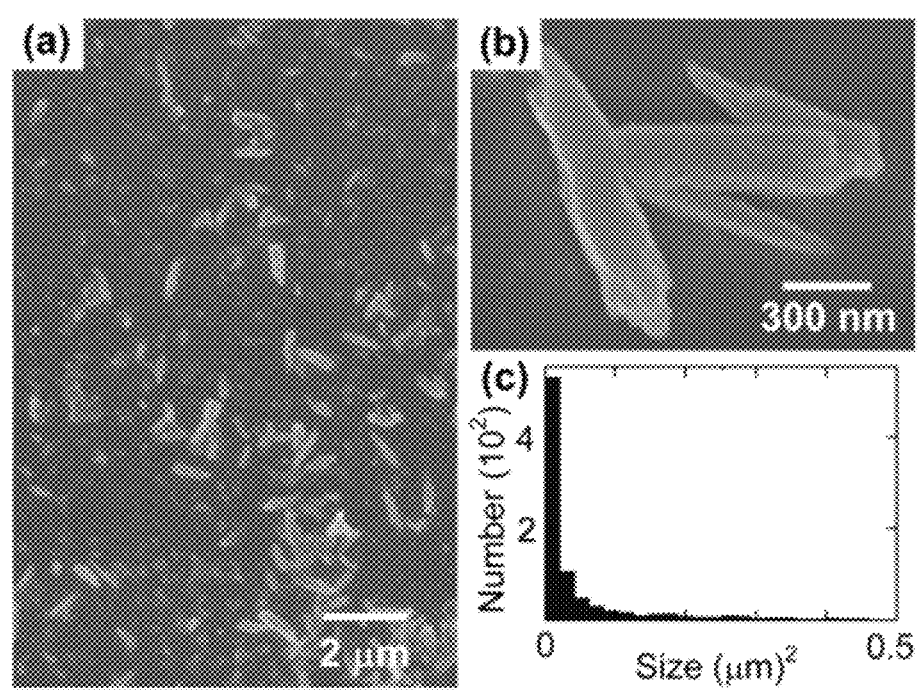
FIG. 14 shows (a) FESEM image of β-hematin crystals. (b) Zoomed in FESEM image of β-hematin crystals. (c) Population distribution of size (area) β-hematin crystals obtained by using Matlab software.

FIG. 14 shows the FESEM image of β-hematin crystals fabricated using the acid-catalyzed method [FIGS. 14(a) and 14(b)] and the size distribution of crystals [FIG. 14(c)]. The fabricated β-hematin crystals are comparable to the size of hemozoin biocrystals found in the ring stage parasites (estimated from the concentration per cell and density of hemozoin) that dominate over other stages in the bloodstream for detection. Close resemblance in the spatial dimensions between the two types of crystals presumably would result in similar SERRS enhancement effect. The minimization of fabricated hemozoin size is to avoid artificially higher enhancement in magnetic field enrichment since larger crystals will have higher magnetic field enrichment as shown in the result later. Hence, the acid catalyzed method is preferred to fabricate smaller crystals over the anhydrously synthesized β-hematin or in the biochemically cloned hemozoin, although the resulted crystals may have lower crystallinity and smaller sizes.

Figure 15:
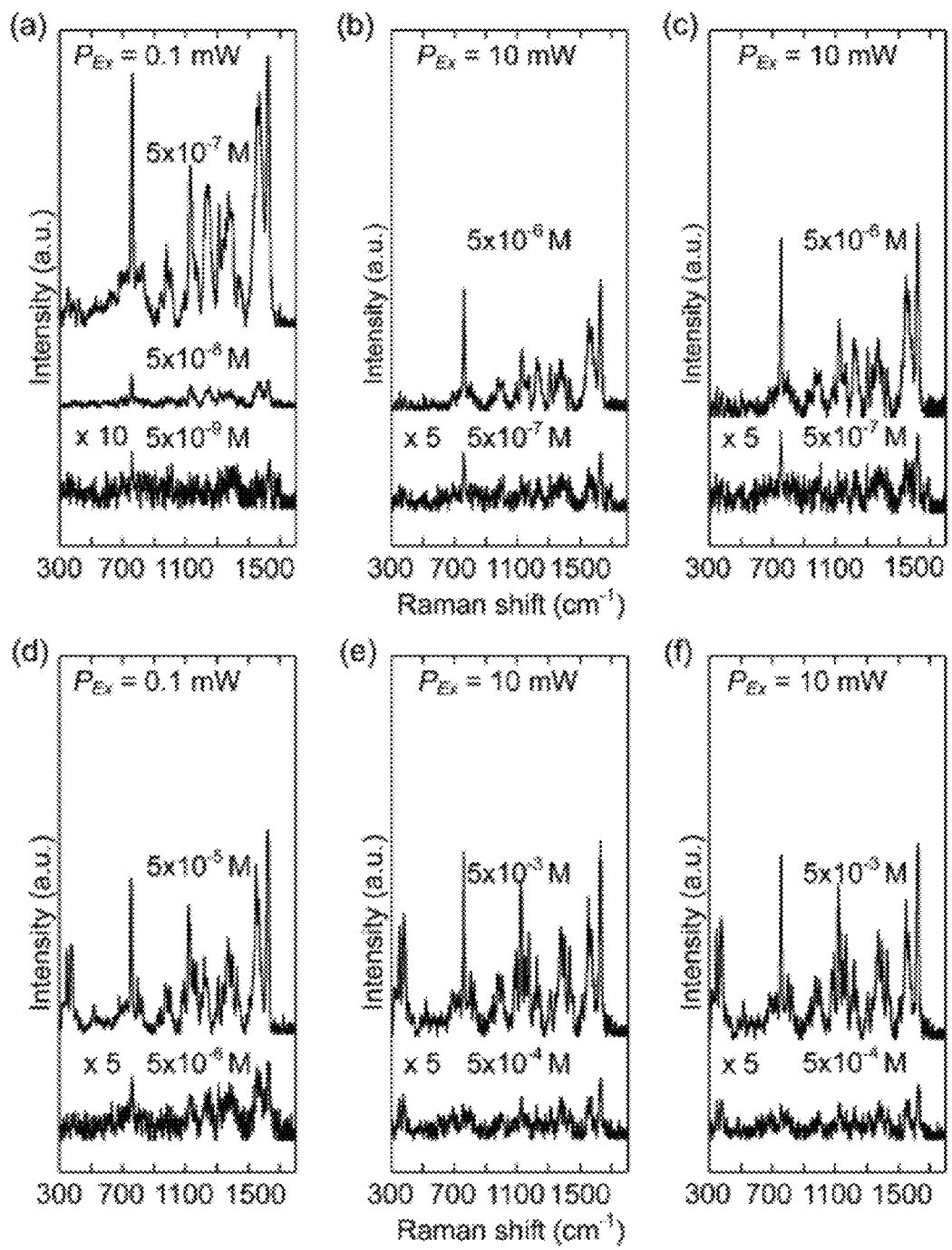
FIG. 15 Magnetic field-enriched spectra of β-hematin crystals in a magnetic field (a) with $Fe_3O_4$@Ag nanoparticles (Concentrations: 5×$10^{-6}$ M to 5×$10^{-9}$M; PEx: 0.1 mW), (b) without and (c) with $Fe_3O_4$ nanoparticles (Concentrations: 5×$10^{-6}$M, and 5×$10^{-7}$ M; $P_{Ex}$: 10 mW). Spectra of β-hematin crystals without magnetic field (d) with $Fe_3O_4$@Ag nanoparticles (Concentrations: 5×$10^{-5}$ M to 5×$10^{-6}$ M; $P_{Ex}$: 0.1 mW), (e) without and (f) with $Fe_3O_4$ nanoparticles (Concentrations: 5×$10^{-3}$ M, and 5×$10^{-4}$ M; $P_{Ex}$: 10 mW). $P_{Ex}$ means the excitation power.

FIG. 15 compares resonance Raman spectra of hematin with [FIGS. 15(a)-(c)] and without [FIGS. 15(d)-(f)] magnetic field enriched strategy at concentrations ranging from $10^{-3}$ M to $5\times10^{-9}$ M. Prominent vibrational features, such as ν8 (based on the electron spin and crystallographic coordination notation tetragonal D4h system for resonance Raman peaks studies on myoglobin) at 345 cm-1, γ6 at 367 cm-1, ν15 at 754 cm-1, ν22 at 1120 cm-1, ν11 at 1551 cm-1, ν2 at 1570 cm-1, and ν10 at 1628 cm-1, are noted in most of these spectra. The locations of these peaks are equal to those reported Raman peaks for hemozoin biocrystals, confirming that the spectral features of β-hematin crystals are equivalent to hemozoin in Raman spectroscopy. The effect of surface enhancement can be clearly distinguished when the SERRS [FIGS. 15(a) and 15(d)] are compared with the RRS measurements [FIGS. 15(b) and 15(e)] and the RRS measurements by using $Fe_3O_4$ nanoparticles [FIGS. 15(c) and 15(f)]. It is also noted that the lowest detectable concentrations of β-hematin for SERRS with $Fe_3O_4$@Ag nanoparticles, RRS, and RRS with $Fe_3O_4$ nanoparticles under magnetic field enrichment are $5\times10^{-9}$ M, $5\times10^{-7}$ M, and $5\times10$-7 M, respectively, and those without magnetic field enrichment are $5\times10^{-6}$ M, $5\times10^{-4}$ M, and $5\times10^{-4}$ M, respectively, where the excitation power in the SERRS measurements was 0.1 mW and that in the RRS measurements was 10 mW.

Discussion

It has been demonstrated the feasibility and significant improvement of magnetic field-enriched SERRS over conventional SERRS for detecting β-hematin crystals at low concentrations. To gain additional insight into Raman enhancement in this technique, the analytical enhancement factor (AEF) in each of the following techniques relative to the RRS measurement of β-hematin crystals without $Fe_3O_4$ nanoparticles was calculated [FIG. 15(e)]:
1. magnetic field-enriched SERRS ($AEF_{magSERRS/RRS;\ \beta\text{-}hema}$),
2. SERRS without magnetic field ($AEF_{SERRS/RRS;\ \beta\text{-}hema}$), and
3. magnetic field-enriched RRS ($AEF_{magRRS/RRS;\ \beta\text{-}hema}$).

These AEFs have been calculated by applying Eq. (7):

$$AEF=(I_{1628,Augmented}/I_{1628,REF})\times(C_{Ref}/C_{Augmented}) \quad (7)$$

where $(I_{1628,\ Augmented}/I_{1628,\ Ref})$, and $(C_{Augmented}/C_{Ref})$ are the ratio of Raman intensity at 1628 cm$^{-1}$, and the ratio of β-hematin concentration, respectively, in the measurements to be evaluated (magnetic field-enriched SERRS, SERRS, or magnetic field-enriched RRS) to those in the reference measurement (RRS). The estimated AEF values are listed as follows: $AEF_{magSERRS/RRS;\ \beta\text{-}hema}\approx2.30\times10^5$, $AEF_{SERRS/RRS;\ \beta\text{-}hema}\approx1.54\times10^3$, and $AEF_{magRRS/RRS;\ \beta\text{-}hema}\approx68$. Hence, the magnetic field enrichment can improve the signal intensities by roughly two orders of magnitude. The three orders of magnitude augmentation in the detection limit between the measurements with and without the magnetic field enriched can be attributed to the reduced noise level in the Raman signal in the magnetic field-enriched measurement.

The enhancement mechanism behind the addition of $Fe_3O_4$@Ag nanoparticles is studied. SERRS signal of β-hematin [FIG. 15(d)] is only exhibited by mixing nanoparticles with the SERS-active silver shell and β-hematin. RRS is resulted for $Fe_3O_4$ nanoparticles and β-hematin mixture [FIG. 15(f)], with RRS signal comparable to that of β-hematin without any nanoparticles [FIG. 15(e)]. This observation also applies to the magnetic field-enriched measurement, with only SERRS enhancement noted in the mixture of $Fe_3O_4$@Ag nanoparticles and β-hematin [FIG. 15(a)], while RRS is exhibited in the β-hematin mixture with [FIG. 15(b)] and without [FIG. 15(c)] $Fe_3O_4$ nanoparticles under a magnetic field. RRS intensities of β-hematin with $Fe_3O_4$ nanoparticles under magnetic field is 1.4 times higher than that without $Fe_3O_4$ nanoparticles, probably attributed to the enhanced aggregation of 3-hematin due to the $Fe_3O_4$ nanoparticles. The spectral shapes are similar in the SERRS and RRS spectra despite the fact that higher intensity is noted in the SERRS spectra. The similarity may be explained by the unchanged chemical structure and symmetry of β-hematin crystals that are magnetically held to the $Fe_3O_4$@Ag nanoparticles. Compared to many other molecules such as R6G, the adsorption of β-hematin crystals onto the Ag surface is weaker thus its SERRS spectrum is less influenced by the adsorption. The similar phenomenon is also observed in other chemicals that have weak interactions with Ag.

It is compared $AEF_{SERRS/RRS}$ for β-hematin with $AEF_{SERS/Raman}$ for R6G, since the two quantities are considered equivalent. The enhancement factor of SERS relative to ordinary Raman for R6G ($AEF_{SERS/Raman;\ R6G}\approx5.77\times106$) is higher than that of the SERRS relative to RRS for β-hematin ($AEF_{SERRS/RRS;\ \beta\text{-}hema}\approx1.54\times103$), which can be attributed to the larger size of the β-hematin compared R6G molecules, with size (area) at least greater than roughly 30 nm×30 nm (FIG. 14). Nevertheless, aggregates formed between magnetic β-hematin and the $Fe_3O_4$@Ag nanoparticles can still lead to effective SERS activities, similar to the configurations reported in the literature (e.g. localized AEF of about $10^9$ in configuration such as dimers and trimers). In addition, SERS can be observed in β-hematin at a distance from the Ag surface in the aggregation configuration (<40 nm), similar to that in other SERS nanoparticles. The $AEF_{SERRS/RRS;\ \beta\text{-}hema}$ is compensated by the further augmentation in the magnetic field enriched SERRS and RRS measurements, which can be explained by the following effects induced by the magnetic field. First, β-hematin is enriched. Second, more $Fe_3O_4$@Ag nanoparticles are attached to each β-hematin crystal and thus, leading to higher SERRS intensity. The potential mechanisms responsible for these effects are elaborated as follows.

Figure 16:
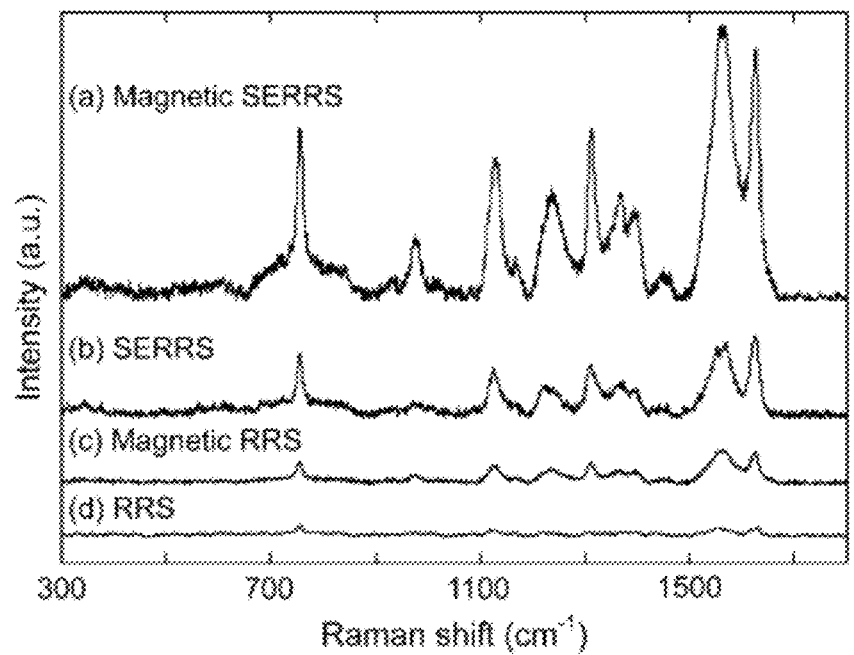
FIG. 16 shows (a) Magnetic field-enriched SERRS and (b) SERRS spectra of β-hematin supernatant obtained by centrifuging (β-hematin at concentration of $10^{-4}$ M) at an excitation power of 0.1 mW. (c) Magnetic field enriched RRS and (d) RRS spectra of the same β-hematin supernatant at an excitation power of 10 mW.

The enrichment of β-hematin concentrations due to a magnetic field can be interpreted by the fact that paramagnetic β-hematin are attracted much faster to the bottom of the vial by the magnet than unmagnetized crystals without the influence of a magnetic field. Consequently, the concentration of β-hematin will be higher at the laser spot than that without the magnetic field, which has been demonstrated by a value of 68 in $AEF_{magRRS/RRS;\ \beta\text{-}hema}$ for RRS measurements under the influence of a magnetic field in the absence of nanoparticles [FIG. 15(c)]. The magnetic field enrichment effect is more significant in larger β-hematin crystals, as confirmed by our Raman experiment in the β-hematin supernatant after centrifuging (FIG. 16). Higher $AEF_{magRRS/RRS;\ \beta\text{-}hema}$ is observed in the magnetic field-enriched RRS for β-hematin mixture without centrifuging (68 in FIG. 15) than that calculated in the β-hematin supernatant (4 in FIG. 16). Hence, the magnetic field can effectively enrich β-hematin crystals to give rise to strong enhancement.

Figure 17:
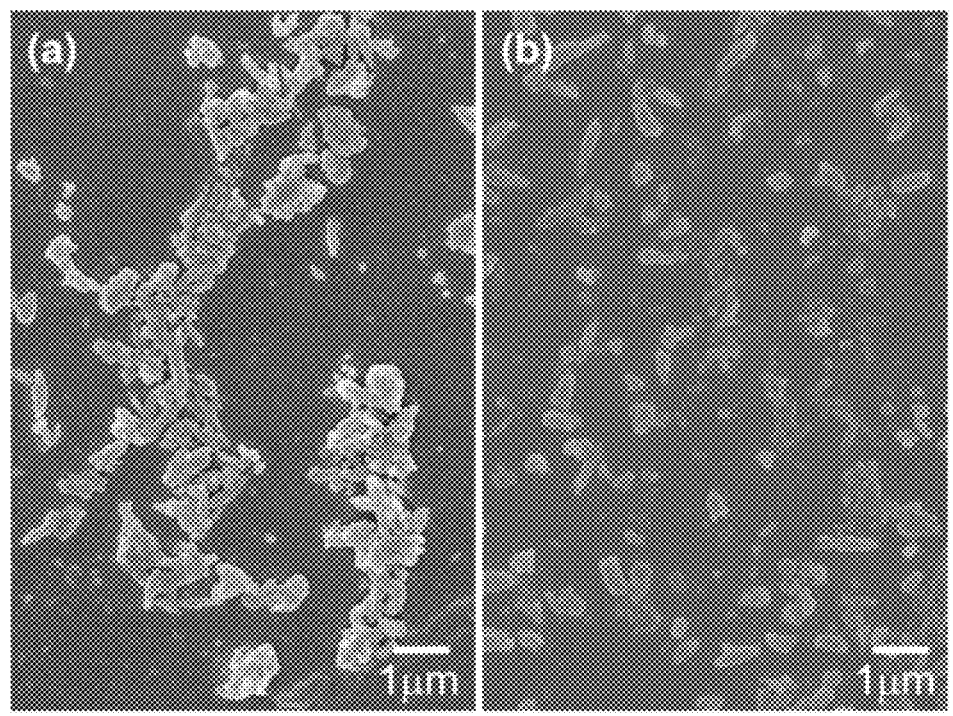
FIG. 17 shows FESEM images of $Fe_3O_4$@Ag nanoparticles and β-hematin crystals (a) with and (b) without the external magnetic field.

More nanoparticle-hematin aggregates are formed by an external magnetic field. FIG. 17 shows that more $Fe_3O_4$@Ag nanoparticles are bound to β-hematin crystals in a magnetic field [FIG. 17(a)] compared to the case without a magnetic field [FIGS. 17(b) and 17(c)]. Since the $Fe_3O_4$ core of the nanoparticles is ferromagnetic, the magnetic field produced by each Fe$_3$O$_4$@Ag nanoparticle attracts adjacent β-hematin crystals [FIGS. 17(*b*) and 17(*c*)]. More Fe$_3$O$_4$@Ag nanoparticles are close or tightly bound to β-hematin crystals under an external magnetic field [FIG. 17(*a*)]. FIG. 17(*d*) shows a schematic physical model for the configurations of Fe$_3$O$_4$@Ag nanoparticles and β-hematin crystals that leads to surface enhancement. For each crystal attached at the contact or in close vicinity (<40 nm) in the gap to the Fe$_3$O$_4$@Ag nanoparticle, known as "hot spots," intense SERS activities occur. Additional hot spots are formed with more aggregations with the application of an external magnetic field. The increased number of nanoparticles-hematin aggregates may be responsible for the further improvement in the AEF$_{magSERRS/RRS;\ β\text{-}hema}$ that is 149 times larger than the AEF$_{SERRS/RRS;\ β\text{-}hema}$, in comparison with that in RRS without the involvement of nanoparticles as in AEF$_{magRRS/RRS;\ β\text{-}hema}$≈68. In contrast, the ratio of EF$_{magSERRS/RRS;\ β\text{-}hema}$ to EF$_{SERRS/RRS;\ β\text{-}hema}$ in β-hematin supernatant (3540/1200≈3) is similar in magnitude to the AEF in the magnetic RRS measurement (AEF$_{magRRS/RRS;\ β\text{-}hema}$≈4), since the β-hematin supernatant contained mostly small crystals that are already attached on the nanoparticles. Therefore, more nanoparticle-hematin aggregates can give further augmentation in Raman signals, in addition to the SERRS and β-hematin enrichment effects.

With the two aforesaid magnetic field induced effects, it is evaluated the detection limit of β-hematin using magnetic field-enriched SERRS by converting β-hematin concentration to the concentration of malaria parasites in blood for practical evaluation. The detection limit of β-hematin concentration at 5×10$^{-9}$ M in the magnetic field-enriched SERRS measurement obtained in this study is equivalent to roughly 30 parasites/μl (considering a hemozoin concentration of about 0.22 pg/cell in the earlier malaria infection at the ring stage and a molecular weight of 1229 g/mol for hemozoin) at the early stage. More importantly, the sensitivity is comparable to other rapid malaria detection techniques for hemozoin detection at later malaria stages, e.g. 10 parasites/μl (with hemozoin concentration at about 0.6 pg/cell), for laser desorption mass spectrometry and automated blood cell counters. With the high sensitivity in the detection of β-hematin in the current configuration without optimization, the magnetic field-enhanced SERRS technique has demonstrated great potential for early malaria diagnosis. The detection sensitivity of our technique could be further improved by optimizing the configuration of the magnetic field and the physical geometry of SERS-active nanoparticles.

Analytical Enhancement Factor Calculation

The analytical enhanced factors are calculated for the following. For rhodamine 6G (R6G) molecules, the SERS AEF of R6G molecules in the nanoparticles solution of iron oxide core coated with silver shell (Fe$_3$O$_4$@Ag) with respect to the ordinary Raman measurement (AEF$_{SERS/Raman;\ R6G}$) has been calculated. For the β-hematin crystals, 1. the equivalent magnetic field enriched SERRS AEF (AEF$_{magSERRS/RRS;\ β\text{-}hema}$), 2. The SERRS AEF without magnetic field (AEF$_{SERRS/RRS;\ β\text{-}hema}$), and 3. the equivalent magnetic field-enriched RRS AEF (AEF$_{magRRS/RRS;\ βhema}$) relative to RRS measurements have been calculated. The AEF in magnetic field-enriched measurement are equivalent AEF, in which the β-hematin concentrations are the concentrations prior to the magnetic field enrichment. These AEFs were calculated from the equation Eq. (8), $$AEF = \frac{I_{\lambda, Augmented}}{I_{\lambda, Ref}} \times \frac{P_{Augmented}}{P_{Ref}} \times \frac{C_{Ref}}{C_{Augmented}} \quad (8)$$

where ($I_{\lambda;\ Augmented}/I_{\lambda;\ Ref}$), ($P_{Augmented}/P_{Ref}$) and ($C_{Augmented}/C_{Ref}$) are the ratios of the Raman intensities at Raman shift of excitation powers, and concentrations in enhanced and referenced measurements.

Calculation of AEF$_{SERS/Raman;\ R6G}$

The AEF$_{SERS/Raman;\ R6G}$ of R6G in Fe$_3$O$_4$@Ag nanoparticle solution can be calculated as, $$AEF = \frac{I_{1365,SERS}}{I_{1365,Raman}} \times \frac{P_{Raman}}{P_{SERS}} \times \frac{C_{RAMAN}}{C_{SERS}} \quad (9)$$

$$= \frac{9135.5}{1584} \times \frac{10\ mW}{0.1\ mW} \times \frac{10^{-2}\ M}{10^{-6}\ M}$$

$$\approx 5.77 \times 10^6$$

where the two numbers 9135.5 and 1584 are the SERS and ordinary Raman intensities of R6G, respectively, at the concentrations of 10$^{-6}$ M and 10$^{-2}$ M, excited at corresponding laser power of 0.1 mW and 10 mW.

Calculation of Equivalent AEF$_{magSERRS/RRS;\ β\_hema}$, AEF$_{SERRS/RRS;\ β\_hema}$, AEF$_{RRS/RRS;\ β\_hema}$ Similarly, the analytical enhancement factors in the measurement of magnetic field-enriched SERRS, SERRS and magnetic field-enriched RRS with reference to the RRS measurement of β-hematin crystals, can be calculated by Eq. (8). Table 1 gives the parameters for the calculation. Note that the equivalent AEFs are calculated in the magnetic field-enriched measurement, since the concentrations stated are concentrations of β-hematin prior to the use of a magnetic field. The AEF values are listed as follows: AEF$_{magSERRS/RRS;\ β\text{-}hema}$≈2.30×10$^5$, AEF$_{SERRS/RRS;\ β\text{-}hema}$≈1.54×10$^3$, and AEF$_{magRRS/RRS;\ β\text{-}hema}$≈68.

Table 2 gives the parameters for the calculation of the analytical enhancement factors in the measurement of magnetic field-enriched SERRS, SERRS and magnetic field enriched RRS with reference to the RRS measurement of β-hematin supernatant after centrifuging. The results are AEF$_{magSERRS/RRS;\ β\text{-}hema}$≈3.54×103, AEF$_{SERRS/RRS;\ β\text{-}hema}$≈1.20×103, and AEF$_{magRRS/RRS;\ β\text{-}hema}$≈4.

TABLE 1

Parameters used in the calculation of the AEF$_{magSERES/RES,β\text{-}hema}$, AEF$_{SERES/RRS,β\text{-}hema}$, and AEF$_{magRRS/RRS,βhema}$ for β-hematin.

| | $I_{1628,\ Augmented}$ (o.u.) | $I_{1628,\ Ref}$ (o.u.) | $P_{Augmented}$ (mM) | $P_{Ref}$ (mM) | $C_{Augmented}$ (μM) | $C_{Ref}$ (mM) | AEF |
|---|---|---|---|---|---|---|---|
| Calculation of AEF$_{magSERRS/RRS,β\text{-}hema}$ | 1494 | 1300 | 0.1 | 10 | 0.5 | 1 | 2.30 × 10$^5$ |
| Calculation of AEF$_{SERRS/RRS,β\text{-}hema}$ | 100 | 1300 | 0.1 | 10 | 5 | 1 | 1.54 × 10$^3$ |

TABLE 1-continued

Parameters used in the calculation of the $AEF_{magSERES/RES,\beta-hema}$, $AEF_{SERES/RRS,\beta-hema}$, and $AEF_{magRRS/RRS,\beta-hema}$ for β-hematin.

| | $I_{1628, Augmented}$ (o.u.) | $I_{1628, Ref}$ (o.u.) | $P_{Augmented}$ (mM) | $P_{Ref}$ (mM) | $C_{Augmented}$ (μM) | $C_{Ref}$ (mM) | AEF |
|---|---|---|---|---|---|---|---|
| Calculation of $AEF_{magRRS/RES,\beta-hema}$ | 442 | 1300 | 10 | 10 | 5 | 1 | 68 |

TABLE 2

Parameters used in the calculation of the $AEF_{magSERRS/RRS,\beta-hema}$, $AEF_{SERRS/RRS,\beta-hema}$, and $AEF_{magRRS}$ or β-hematin supernatant after centrifuging.

| | $I_{1628,Augmented}$(a.u.) | $I_{1628,Ref}$(a.u.) | $P_{Augmented}$(mW) | $P_{Ref}$(mW) | AEF |
|---|---|---|---|---|---|
| Calculation of $AEF_{magSERRS/RRS,\beta-hema}$ | 20040 | 566 | 0.1 | 10 | $3.54 \times 10^3$ |
| Calculation of $AEF_{SERRS/RRS,\beta-hema}$ | 6768 | 566 | 0.1 | 10 | $1.20 \times 10^3$ |
| Calculation of $AEF_{magRRS/RRS,\beta-hema}$ | 2264 | 566 | 10 | 10 | 4 |

By "comprising" it is meant including, but not limited to, whatever follows the word "comprising". Thus, use of the term "comprising" indicates that the listed elements are required or mandatory, but that other elements are optional and may or may not be present.

By "consisting of" is meant including, and limited to, whatever follows the phrase "consisting of". Thus, the phrase "consisting of" indicates that the listed elements are required or mandatory, and that no other elements may be present.

The disclosures illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure. Thus, it should be understood that although the present disclosure has been specifically disclosed by preferred embodiments and optional features, modification and variation of the disclosures embodied therein herein disclosed may be resorted to by those skilled in the art, and that such modifications and variations are considered to be within the scope of this disclosure.

By "about" in relation to a given numerical value, such as for temperature and period of time, it is meant to include numerical values within 10% of the specified value.

The disclosure has been described broadly and generically herein. Each of the narrower species and sub-generic groupings falling within the generic disclosure also form part of the disclosure. This includes the generic description of the disclosure with a proviso or negative limitation removing any subject matter from the genus, regardless of whether or not the excised material is specifically recited herein.

Other embodiments are within the following claims and non-limiting examples. In addition, where features or aspects of the disclosure are described in terms of Markush groups, those skilled in the art will recognize that the disclosure is also thereby described in terms of any individual member or subgroup of members of the Markush group.

The invention claimed is:

1. A method of diagnosing malaria infection in a patient by Surface Enhanced Raman Spectroscopy (SERS), comprising:
    obtaining a sample from said patient;
    mixing the sample with a suspension of magnetic nanoparticles, wherein said magnetic nanoparticles adsorb hemozoin present in the sample onto their surface;
    obtaining the SERS spectra of the sample;
    subjecting the sample and suspension of magnetic nanoparticles to a magnetic field prior to and/or during obtaining the SERS spectra of sample, wherein said subjecting comprises applying a magnetic force in a direction of the force of gravity by manipulating a direction of the magnetic field; and
    correlating the obtained SERS spectra to the presence or amount of hemozoin in the sample, wherein the presence of hemozoin is indicative of malaria infection, wherein the magnetic nanoparticles comprise a core-shell structure, the shell of the core-shell structure comprises a SERS active metal, and the hemozoin adsorbs onto surfaces of the core-shell structures of the magnetic nanoparticles.

2. The method of claim 1, wherein obtaining the SERS spectra comprises exciting with a laser source the sample mixed with the suspension of magnetic nanoparticles.

3. The method of claim 2, wherein subjecting the sample and suspension of magnetic nanoparticles to the magnetic field includes subjecting the sample and suspension of magnetic nanoparticles to the magnetic field prior to and/or during excitation with the laser source.

4. The method of claim 2, wherein exciting the sample with a laser source comprises exciting the sample with a laser source having a resonant wavelength for hemozoin.

5. The method of claim 4, wherein exciting the sample with a laser source comprises exciting the sample with a laser source having a wavelength of about 633 nm.

6. The method of claim 1, wherein the core of the core-shell structure comprises a magnetic material.

7. The method of claim 1, wherein the core of the core-shell structure comprises $Fe_3O_4$ core and the shell of the core-shell structure comprises Ag.

8. The method of claim 1, wherein the magnetic nanoparticles have magnetic surfaces, respectively, and mixing the sample with the suspension of magnetic nanoparticles includes adsorbing hemozoin present in the sample onto the metallic surfaces at least some of the magnetic nanoparticles.

9. The method of claim 1, wherein the magnetic nanoparticles each have a magnetic core and a metallic shell directly bonded to the magnetic core, and mixing the sample with the suspension of magnetic nanoparticles includes adsorbing hemozoin present in the sample onto metallic surfaces at least some of the magnetic nanoparticles.

* * * * *